(12) United States Patent
Foos et al.

(10) Patent No.: US 9,357,974 B2
(45) Date of Patent: Jun. 7, 2016

(54) INTEGRATED PORTABLE DIGITAL X-RAY IMAGING SYSTEM

(75) Inventors: David H. Foos, Rochester, NY (US); William J. Sehnert, Fairport, NY (US); Zhimin Huo, Pittsford, NY (US); Hui Luo, Rochester, NY (US); Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 366 days.

(21) Appl. No.: 12/967,418

(22) Filed: Dec. 14, 2010

(65) Prior Publication Data

US 2011/0110496 A1 May 12, 2011

Related U.S. Application Data

(63) Continuation-in-part of application No. 12/581,912, filed on Dec. 20, 2009, now Pat. No. 8,021,045.

(60) Provisional application No. 61/108,630, filed on Oct. 27, 2008.

(51) Int. Cl.
*A61B 6/04* (2006.01)
*A61B 6/00* (2006.01)
*G06F 19/00* (2011.01)

(52) U.S. Cl.
CPC .............. *A61B 6/462* (2013.01); *A61B 6/4405* (2013.01); *A61B 6/463* (2013.01); *A61B 6/465* (2013.01); *A61B 6/563* (2013.01); *G06F 19/321* (2013.01); *G06F 19/3406* (2013.01); *A61B 6/482* (2013.01)

(58) Field of Classification Search
CPC .................................. A61B 6/542; A61B 6/54
See application file for complete search history.

(56) References Cited

U.S. PATENT DOCUMENTS

| | | | |
|---|---|---|---|
| 6,475,146 B1 | 11/2002 | Frelburger et al. | |
| 7,006,600 B1 | 2/2006 | Krema et al. | |
| 7,016,467 B2 | 3/2006 | Brooks | |
| 7,038,588 B2 | 5/2006 | Boone et al. | |
| 7,309,159 B2 | 12/2007 | Watanabe | |
| 7,343,565 B2 | 3/2008 | Ying et al. | |
| 7,438,470 B2 | 10/2008 | Koren | |
| 7,502,445 B2 | 3/2009 | Shi et al. | |
| 7,549,961 B1 | 6/2009 | Hwang | |
| 7,573,034 B2 | 8/2009 | Heath et al. | |
| 2004/0086077 A1 | 5/2004 | Moriyama | |
| 2004/0146142 A1* | 7/2004 | Maijala | 378/102 |
| 2005/0100208 A1* | 5/2005 | Suzuki et al. | 382/157 |
| 2005/0226375 A1* | 10/2005 | Eberhard et al. | 378/62 |
| 2005/0265267 A1 | 12/2005 | Hwang | |
| 2006/0274928 A1* | 12/2006 | Collins et al. | 382/132 |
| 2007/0025503 A1* | 2/2007 | Hemmendorff | 378/37 |
| 2007/0036268 A1* | 2/2007 | Matsuno | 378/98.2 |
| 2007/0189462 A1 | 8/2007 | Spahn | |
| 2008/0103509 A1 | 5/2008 | Goldbach | |
| 2008/0144777 A1 | 6/2008 | Wilson | |
| 2009/0041325 A1 | 2/2009 | Luo | |
| 2009/0214099 A1 | 8/2009 | Merlet | |
| 2009/0274272 A1 | 11/2009 | Stanton et al. | |

* cited by examiner

*Primary Examiner* — Hoon Song

(57) ABSTRACT

A method for processing a radiographic image of a patient, executed at least in part on a host processor, initiates exposure in response to an instruction entered from an operator console and obtains radiographic image data from a digital detector that is subjected to the exposure. The obtained radiographic image data is analyzed according to a set of predefined criteria for diagnostic suitability of the image. One or more results of the diagnostic suitability analysis at the operator console is indicated and a listing of one or more corrective actions at the operator console according to the indicated results is provided.

16 Claims, 23 Drawing Sheets

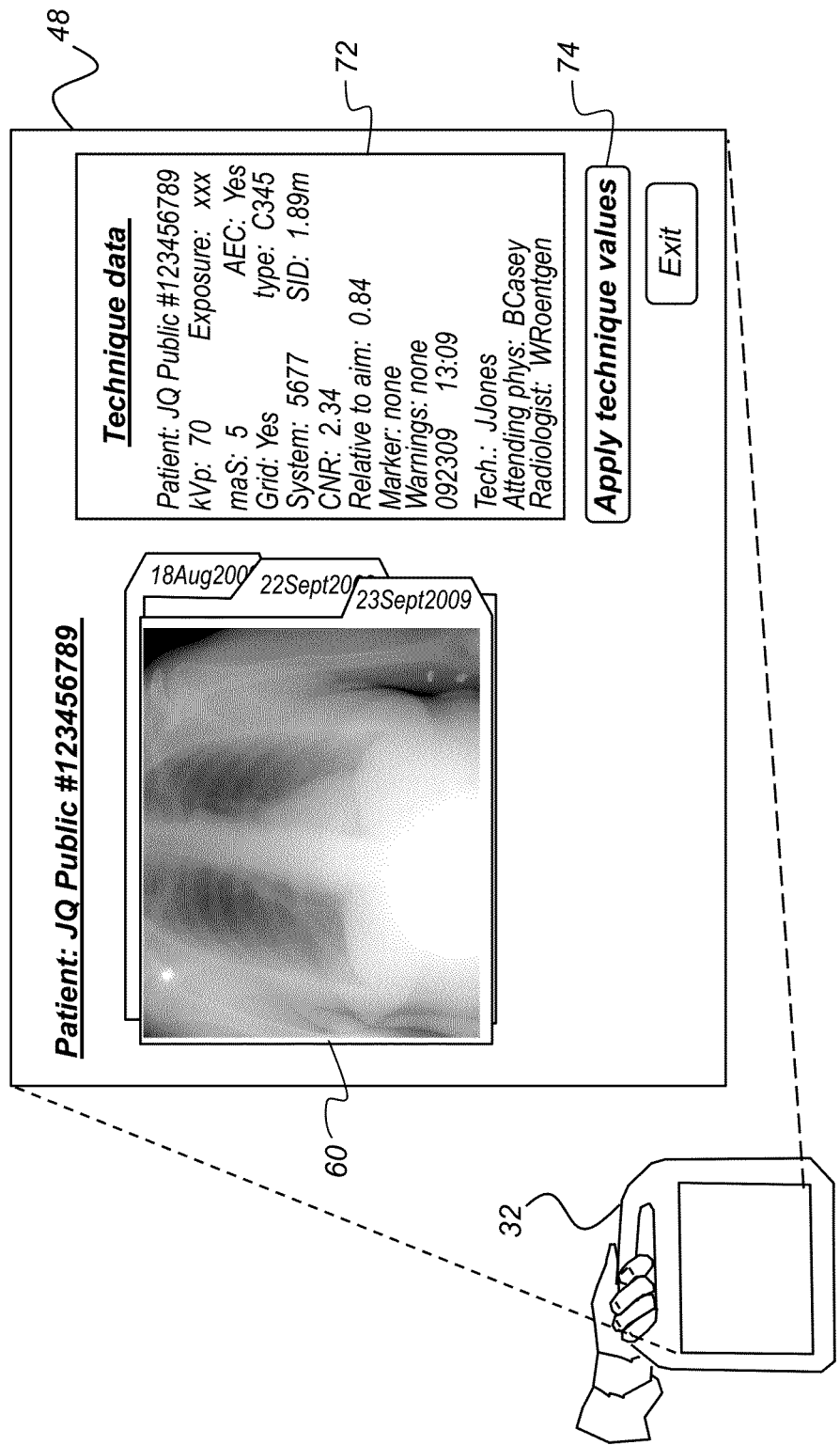

INTEGRATED PORTABLE DIGITAL X-RAY IMAGING SYSTEM

CROSS REFERENCE TO RELATED APPLICATIONS

This is a Continuation-in-Part of commonly assigned U.S. patent application Ser. No. 12/581,912 entitled "INTEGRATED PORTABLE DIGITAL X-RAY IMAGING SYSTEM", in the names of David H. Foos et al., filed Dec. 20, 2009, now U.S. Pat. No. 8,021,045 which claims priority to U.S. Ser. No. 61/108,630, provisionally filed on Oct. 27, 2008, entitled "INTEGRATED PORTABLE DIGITAL X-RAY IMAGING SYSTEM", in the names of David H. Foos et al., both of which are incorporated herein by reference.

FIELD OF THE INVENTION

The invention relates generally to medical imaging and in particular to portable X-ray imaging systems. More specifically, the invention relates to a digital X-ray imaging system that integrates imaging, quality control, and data access functions for improved delivery of diagnostic imaging services.

BACKGROUND OF THE INVENTION

Portable chest radiography is a widely performed radiographic exam in the intensive care unit (ICU). Radiographs of patients in the ICU are captured for a number of reasons, including verification of the placement of life support tubing, line, wires, sensors, and related devices and as part of routine monitoring of a patient's condition.

Flat panel digital radiography (DR) systems are rapidly being introduced into the portable x-ray imaging environment. Advantageously, DR receivers directly convert radiation energy received into digital data, without the need for separate scanning or processing equipment. Because these devices generate image data directly, they are able to provide both a high-resolution image for diagnostic purposes and a lower-resolution preview image that can he used in the clinical environment and for quality control (QC) purposes, facilitating workflow for radiographic technologists in the ICU. Lower resolution images, for example, can be used to quickly provide sufficient information about the positioning of tubing and other life support devices needed in intensive care situations.

Currently, portable DR systems include a portable x-ray machine that generates x-ray radiation, a flat panel DR receiver or detector that is tethered by cable to the portable x-ray machine, a host computer for processing the captured image, and a monitor for assisting image QC. In general, however, existing portable x-ray systems are self contained, tending to be somewhat bulky and inflexible.

In a typical workflow for portable radiography, a technologist is provided with a hard-copy worklist that indicates imaging requirements for various patients in the ICU. The technologist captures the images of all patients on the worklist, then at some convenient opportunity (usually after completing the rounds), downloads the captured images to a PACS (Picture Archive Communications System) for subsequent clinical and diagnostic interpretation. Unfortunately, this conventional workflow pattern can sometimes be poorly suited to the requirements of patient care. The need to upload image data to the PACS or other archive system means that interpretation of the obtained images cannot be performed on-site, but requires coordination with off-site diagnosticians. Urgent care situations require personal intervention and are handled as exceptions rather than accommodated in the workflow. It can be difficult for the clinical staff to determine the status of a worklist request until some time after the image is obtained. There can be an undesirable delay in obtaining response information for problems of tube and line placement. Significant information that can help to guide the imaging process is not made available to the technologist unless it is provided in the worklist data. In addition, quality control (QC) suffers, since the technologist must wait for off-site processing and response in order to determine whether or not an obtained image is usable for diagnostic purposes.

There have been a number of attempts to improve the delivery of portable radiography services in the ICU environment and to provide bedside support for interpreting imaging results and improving patient care. For example, commonly assigned U.S. Pat. No. 7,573,034 entitled "MOBILE RADIOGRAPHY IMAGE RECORDING SYSTEM" to Heath et al. describes a portable radiography system with a network connection for providing an electronic worklist request, for helping to control various imaging functions, for accessing patient records, and for collecting information related to image capture. U.S. Pat. No. 7,016,467 entitled "MOBILE DIGITAL RADIOGRAPHY X-RAY APPARATUS AND SYSTEM" to Brooks describes a portable digital radiography system with a computer for control of the image capture process and for uploading image data from a DR detector to a networked Picture Archiving and Communications System (PACS) or other archive system.

While solutions such as these can help to improve the delivery and efficiency of mobile DR imaging for ICU and other environments, however, further improvements to workflow and more effective delivery of imaging services are still needed. With existing solutions, for example, the technologist does not have ready access to some types of information that can help to provide images that are more acceptable and useful to the diagnostician. This can include, for example, information on prior images obtained and on the imaging techniques used for earlier exams. Workflow remains cumbersome and assignment of technologist tasks still remains a largely manual process in many ICU environments. It can be difficult for the technologist to determine what is needed for each patient and to prioritize the sequence of images that are needed accordingly. There is still a tenuous link between useful information, such as technique settings used previously, and what is needed in order to obtain a new image for the same patient.

Overall, the need for improved support for bedside personnel has not been addressed by conventional solutions, so that considerable back-and-forth communications with off-site staff is often necessary in order to detect problems, such as tube positioning problems. Systems that perform such complex image analysis functions often require the full-resolution image and employ considerable computing power and are designed to show results on high-resolution displays that are used for diagnostic purposes rather than for quick clinical assessment. Conventional approaches have failed to take advantage of the full range of information about the patient and about patient images that can be made available to the imaging technologist and to the ICU staff.

Yet another shortcoming of mobile DR systems relates to lack of information to the technician on the clinical condition of the patient and diagnostic suitability of the image obtained. This type of information would he particularly helpful in the mobile DR environment, such as in ICU and other urgent care facilities, allowing the technician to know of problems as soon as possible and helping to provide input for corrective action.

Thus, while some advances have been made, there is a need for a portable digital x-ray imaging system that more effectively supports the requirements of ICU imaging and the needs of bedside clinical personnel.

SUMMARY OF THE INVENTION

It is an object of the present invention to advance the art of diagnostic imaging and workflow using portable x-ray imaging systems. It is a further object of the present invention to provide clinical personnel with improved tools for bedside analysis of a patient's condition using information obtained from diagnostic images and other diagnostically relevant data. With these objects in mind, the present invention provides a method for processing a radiographic image of a patient, executed at least in part on a host processor, the method comprising: initiating exposure in response to an instruction entered from an operator console; obtaining radiographic image data from a digital detector that is subjected to the exposure; analyzing the obtained radiographic image data according to a set of predefined criteria for diagnostic suitability of the image; indicating one or more results of the diagnostic suitability analysis at the operator console; and providing a listing of one or more corrective actions at the operator console according to the indicated results.

A feature of the present invention is the use of one or more detachable displays that provide the combined functions of image display surfaces, information displays, and data entry work-pads for providing instructions and for recording and displaying patient information.

It is an advantage of the present invention that it provides a portable integrated solution for diagnostic imaging in ICU and other urgent care clinical environments.

It is a further advantage of the present invention that it provides a mechanism for alerting an operator to a detected condition related to image suitability and offers information on possible corrective action according to the condition detected.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 5I is a plan view showing a mode of operation for displaying technique data used for earlier images of the patient.

DETAILED DESCRIPTION OF THE INVENTION

Figure 1:
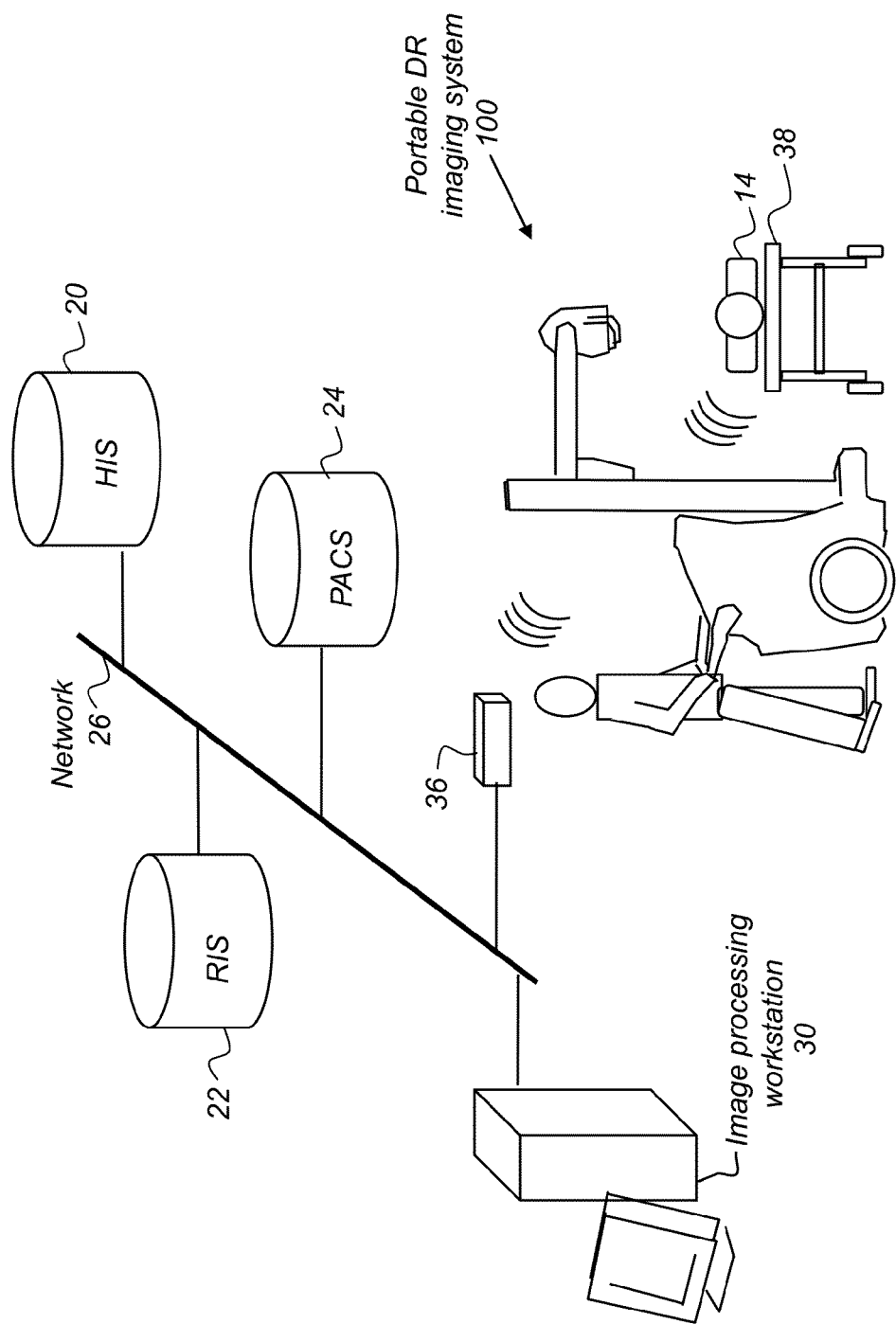
FIG. 1 shows a mobile digital radiography system according to an embodiment of the present invention.

The following is a detailed description of the preferred embodiments of the invention, reference being made to the drawings in which the same reference numerals identify the same elements of structure in each of the several figures.

The schematic block diagram of FIG. 1 shows a mobile digital radiography system 100 that obtains images of a patient 14 in an ICU or other facility and communicates with a number of medical archiving and radiology databases over a network 26. Among the databases that communicate over network 26 are a Hospital Information System (HIS) 20, a Radiologist Information System 22, and a PACS 24. In addition, one or more optional image processing workstations 30 also receive and process images from mobile digital radiography system 100. Mobile digital radiography system 100 has a wireless interface 36 to network 26, typically connecting to a wireless hub or similar data communications interface device. The use of a wireless interface, while not essential to system operation, offers significant advantages for system usability, flexibility, and information access, as described subsequently.

Figure 2:
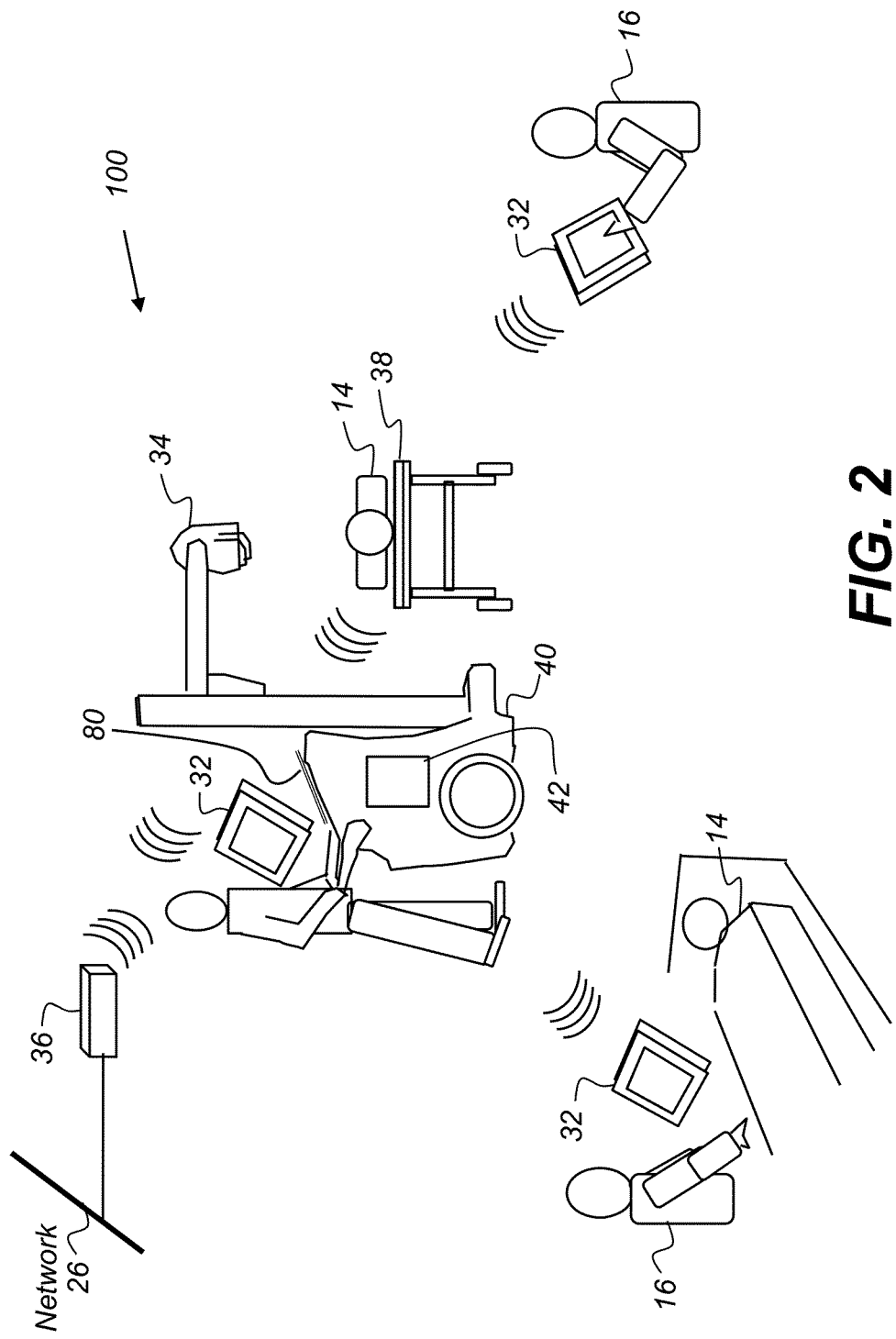
FIG. 2 shows distributed access to the mobile digital radiography system for interpreting or entering information.

FIG. 2 shows a schematic block diagram of mobile digital radiography system 100 in one embodiment. A cart 40 has an x-ray source 34 with the necessary generator and related components for passing x-ray radiation through a portion of the patient's body and on to a DR detector 38. A computer 42, shown within cart 40 in this embodiment, provides the control logic for controlling a number of functions, including controlling the x-ray generation from x-ray source 34, obtaining the digital image data from DR detector 38, and controlling the transfer of data with network 26 and with one or more display interface units 32 that provide an operator interface display. An optional secondary display 80, such as a high-resolution display monitor, is also provided as part of cart 40.

As shown in FIG. 2, a number of detachable display interface units 32 can be used as portable operator consoles of mobile digital radiography system 100 for communication of patient images, patient data and history, instructions, and other data. Display interface unit 32 provides access to mobile digital radiography system 100 in a number of ways. The technologist uses display interface unit 32 as an operator console for obtaining workflow sequence instructions, obtaining information relevant to obtaining a suitable image for each patient, for entering of instructions for controlling the imaging apparatus itself such as for initiating exposure, and for initial quality control (QC) checks of image quality. An attending physician 16 uses display interface 32 to enter instructions and work orders for the image or images needed for a particular patient. The ICU staff use display interface 32 to check the status of imaging requests and to obtain notification that requested images have been obtained. Display interface 32 also serves for interpretation of the patient condition for another physician 16 at the bedside, allowing a comparison with data from prior examinations and allowing interpretation of proper positioning of tubing or other lines, for example.

Figure 3:
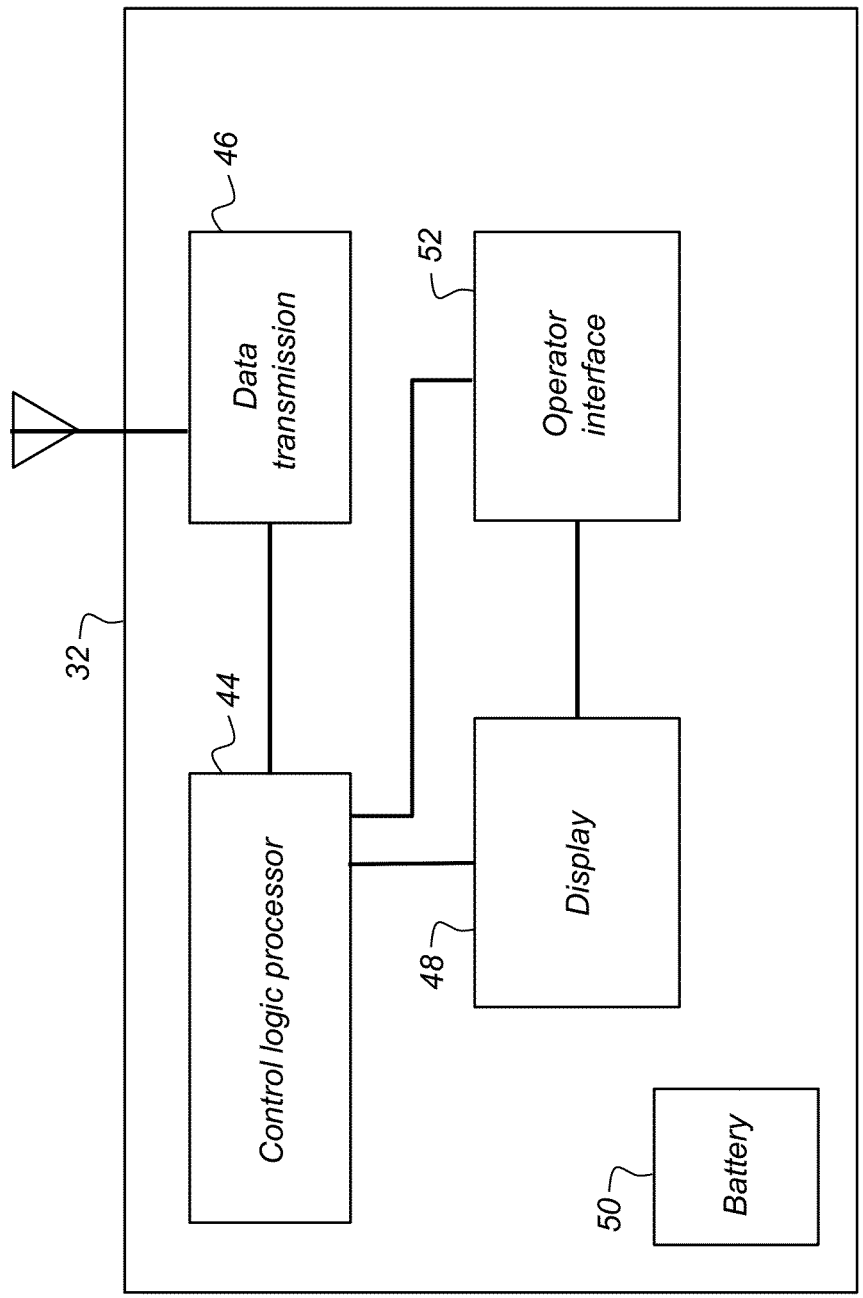
FIG. 3 is a schematic diagram of a display interface unit in one embodiment.

FIG. 3 is a schematic diagram showing components of display interface unit 32 in one embodiment. Display interface unit 32 provides a housing adapted to be held by an operator of the digital radiography system. Its housing encloses the logic processing components, an operator interface display 48, the means for receiving image and other patient data in either a wireless or a cabled mode, and the means for comparing data in some way. Display interface unit 32 also provides a number of utilities for aiding bedside interpretation, as described in more detail subsequently. Operator interface display 48 may he any suitable display type, such as a liquid-crystal or other compact display type. For command entry, a touchscreen or keypad (not shown) is used. A control logic processor 44 provides the needed control logic at least for basic display interface unit 32 functions, including control of operator interface display 48 and data transmission to and from a wireless interface 46. A battery 50 provides on-board power for display interface unit 32 operation. Preferably, battery 50 is a rechargeable battery, needed only when display interface unit 32 is detached from cart 40 (FIG. 2). Control logic processor 44 is a separate microprocessor or similar logic circuitry device in one embodiment, coordinating its control functions with computer 42 on cart 40. In another embodiment, control logic processor 44 provides all of the needed control logic for the complete mobile digital radiography system.

Wireless connection is advantageous and practical for the bedside environment; however, optional data cable and power cable (not shown) are provided in one embodiment, enabling use of display interface unit 32 where battery power fails or where the wireless communication link is not operating properly, such as due to noise from external equipment, for example.

Figure 4:
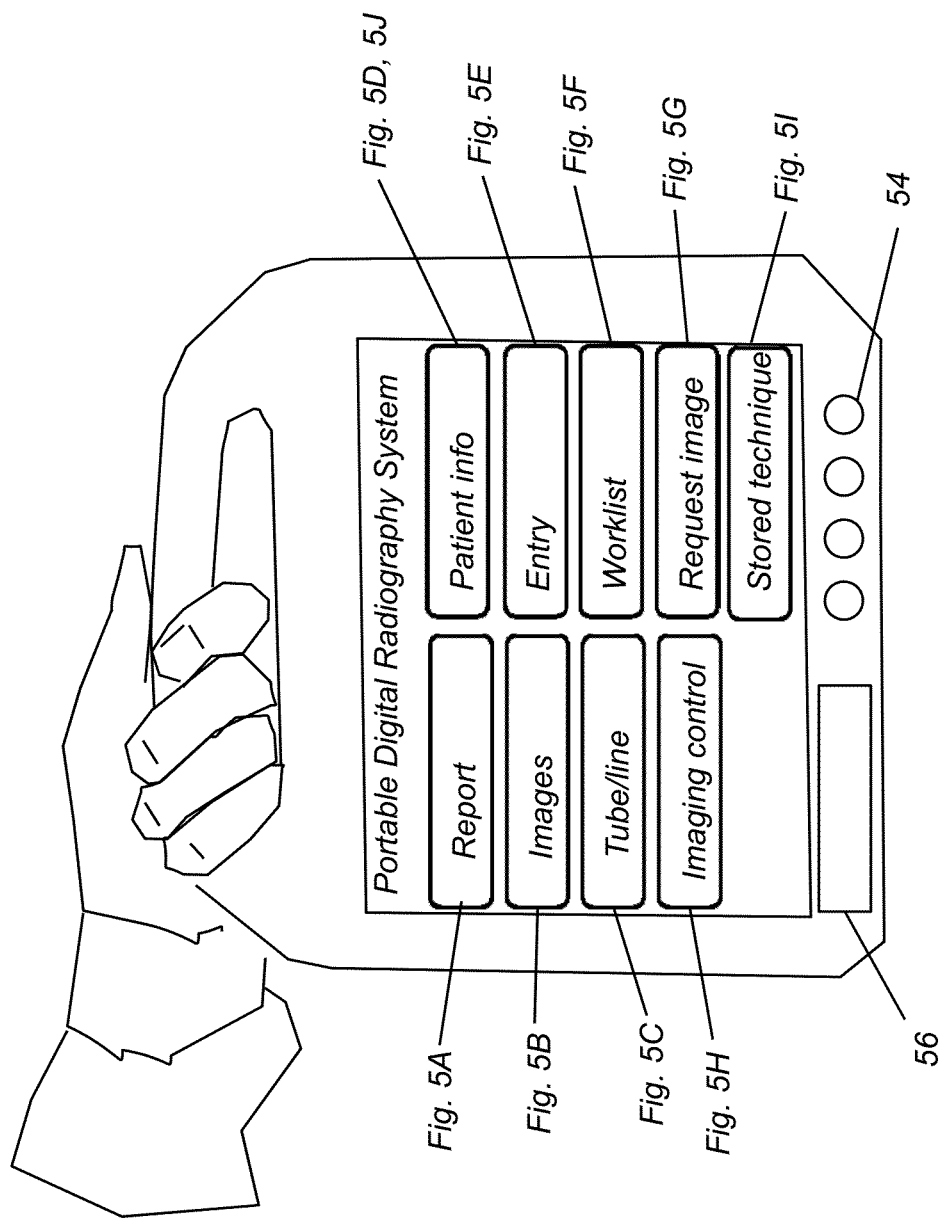
FIG. 4 is a plan view showing a hand-held display interface unit detachable from the mobile digital radiography system.

FIG. 4 shows a hand-held display interface unit 32 that is detached from mobile digital radiography system 100 and shows a displayed menu of exemplary control and reporting functions for display in different areas of this device. The user selects one of the available operating modes, such as by touchscreen entry or using one or more controls 54 or a keypad 56 that are mounted on or otherwise associated with display interface unit 32. In an alternate embodiment, audible instructions are used to select various display and control options. A mouse or other pointer could alternately be used to enter instructions and responses using display interface unit 32. Other known user interface utilities could he employed for manipulating objects on the screen, including cascaded displays or tabs and including slide-away images or displays that respond to operator touch for panning or changing position, for example.

The overall function of display interface unit 32 as a clinical tool includes aiding interpretation of a patient's condition. This can be distinguished from diagnosis, which can require high-resolution displays and image processing of the complete set of image data and which is generally performed on high-end computer workstations. By comparison, clinical interpretation functions can be performed by viewing images that are presented at a relatively lower image resolution, but that have sufficient information to guide timely treatment and urgent care requirements, such as those typical to the ICU environment.

Figure 5A:
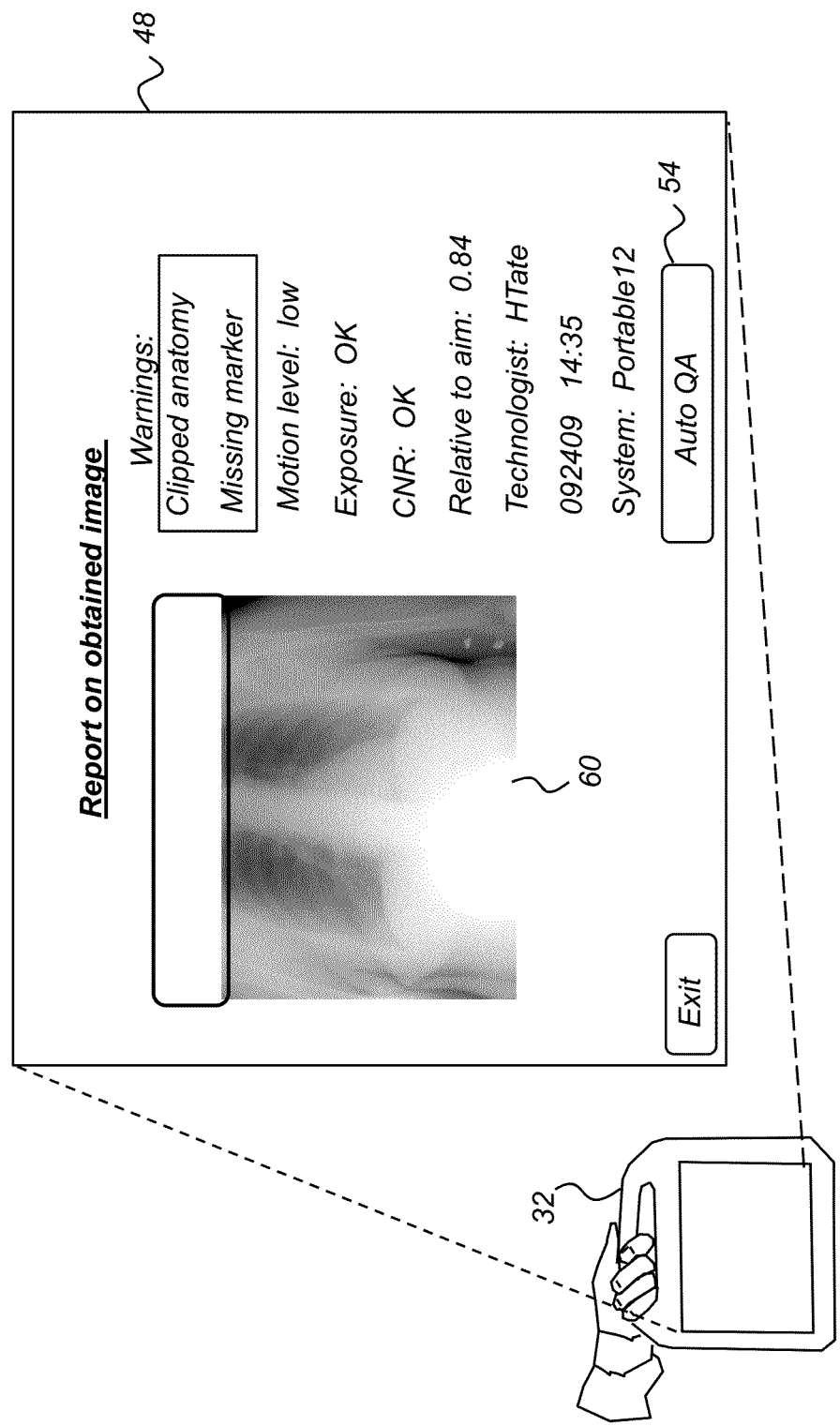
FIG. 5A is a plan view showing a mode of operation for imaging reporting.

By way of example and not of limitation, FIGS. 5A through 5J show various operational modes of display interface unit 32. In FIG. 5A, an image reporting mode is shown. This mode may display a reduced-resolution version of an obtained image 60 and alerts the operator to a detected error or problem that concerns an image previously taken. For example, problems such as clipped anatomy, missing markers, excessive exposure, excessive motion, image artifacts, or other imaging anomalies can be detected and shown, following automatic processing. These can he detected by image processing that is performed by control logic processor 44 (FIG. 3), or by computer 42 (FIG. 2), or by networked image processing workstation 30 (FIG. 1). Imaging characteristics such as Contrast to Noise Ratio (CNR) and exposure levels can also be analyzed and reported at any suitable processor in the image acquisition and processing chain. The image report can also display data such as image exposure relative to an aim exposure level. Information identifying the technologist and system can be useful for obtaining further data or clarification about the exam. An optional control 54 also enables automatic quality assurance routines to he executed on the obtained image data, with reports provided for display.

Figure 5B:
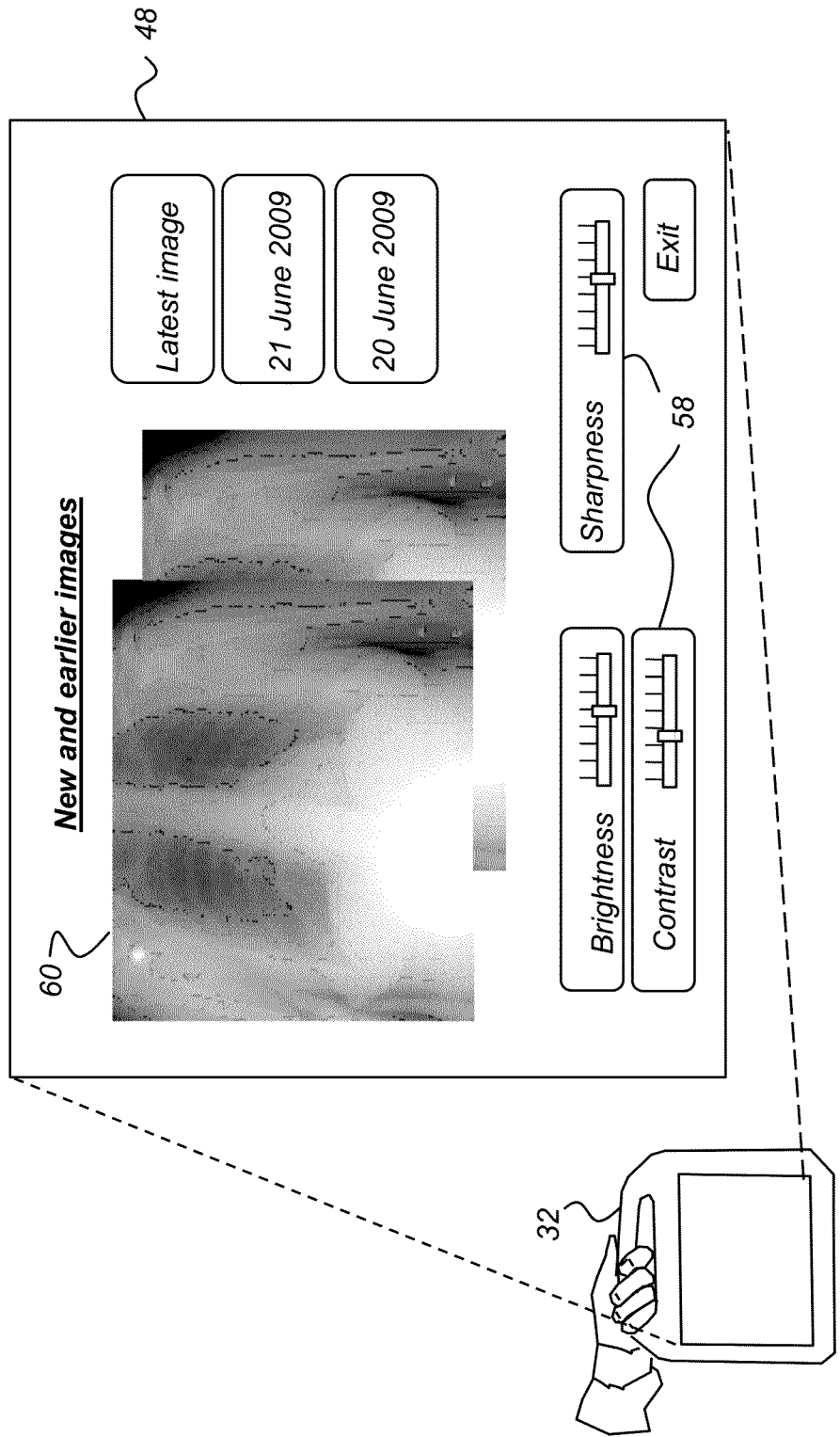
FIG. 5B is a plan view showing a mode of operation for displaying one or more images for the same patient.

The plan view of FIG. 5B shows a display mode for displaying one or more images 60 that have been obtained for the same patient, such as at different times and locations. Using this tool with wireless access to image databases, patient images as well as patient history can he tracked and made available to the attending medical personnel at the patient bedside, without the need for separate requests of patient records. This helps to aid bedside interpretation of a patient's condition by allowing comparison of data from prior and current examinations, for example.

In addition to patient history, display mode also allows display of images with different image processing treatment. Even at the lower-resolution levels provided for such a hand-held device, some imaging characteristics such as overall contrast and image consistency can be visually evaluated.

Controls 58 in FIG. 5B provide mechanisms for adjusting brightness, contrast, sharpness of images, and other image attributes that control display presentation. Automatic processing can alternately he used for any of these and other image attributes. Significant changes in patient condition can be detected by a processor at any point along network 26 (FIG. 1) for reporting to the attending physician in the ICU using this feature. Functions for automatic processing include various features for computer-aided diagnosis and for pneumothorax enhancement in one embodiment. Image comparison can he automatically performed and the results used to provide data as a basis for providing useful clinical information. Images can be displayed side by side or in overlapping windows as shown in FIG. 5B, enabling quick comparison for diagnostic assessment as well as for evaluating rendering consistency.

Figure 5C:
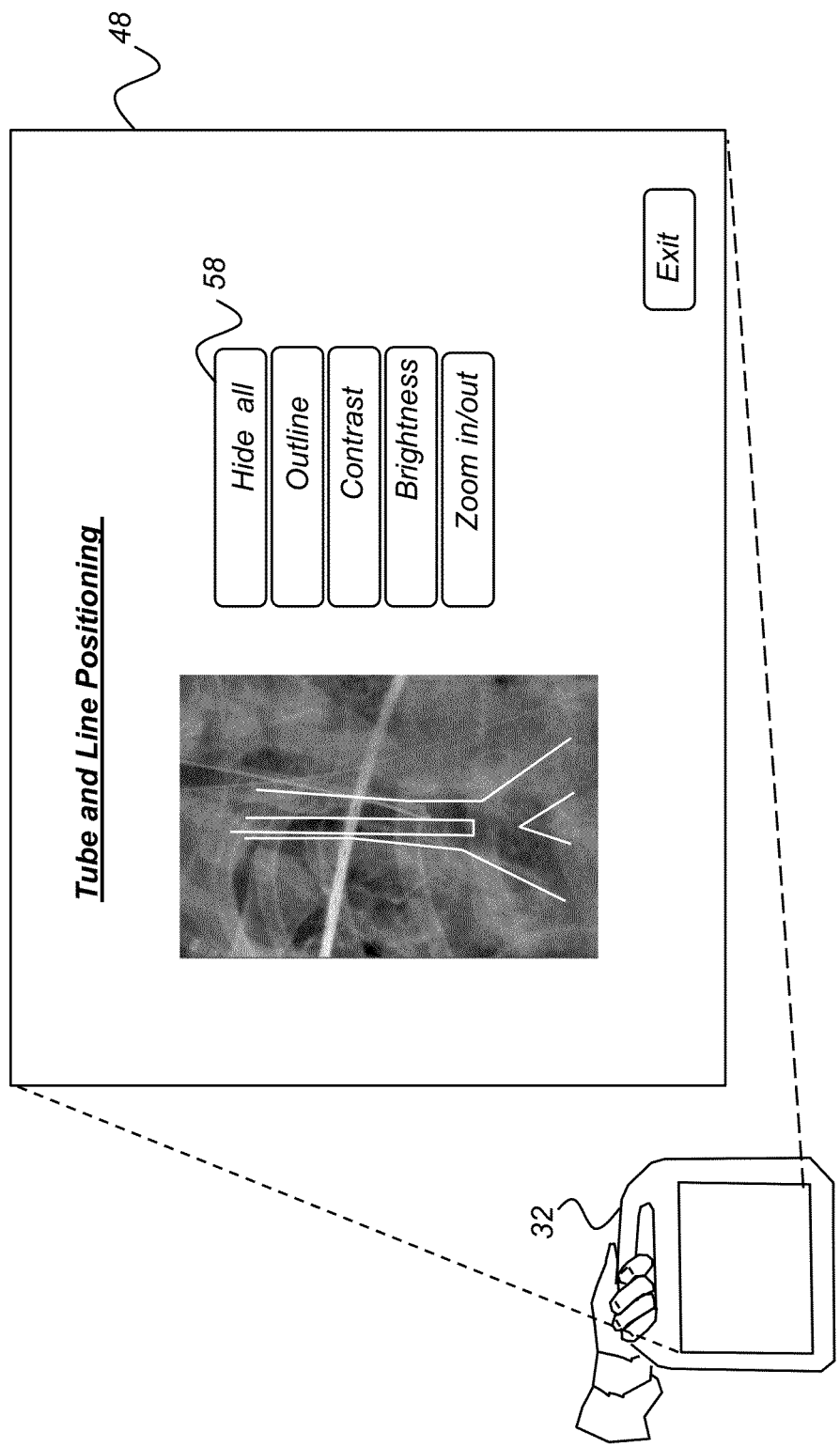
FIG. 5C is a plan view showing a mode of operation for displaying tubing and line position.

FIG. 5C shows the use or display interface unit 32 for displaying various life support line visualizations that have been automatically generated, such as tubing and line position and catheter placement. Image processing algorithms that support this function can be provided at any suitable processor in the network, including at control logic processor 44 within display interface unit 32. However, because this detection can be a complex computational task requiring substantial control logic and memory resources, it is more likely that tubing detection would be implemented at image processing workstation 30 (FIG. 1) and results formatted for low-resolution display and downloaded to display interface unit 32 when requested. A set of controls 58 are provided for manipulating the image display to help improve the visibility of lines and tubing in the radiographic image. In one embodiment, visualization settings for life support line presentations can be pre-set, so that settings and selections found most readily usable to the attending medical team can be employed, such as using them as default settings, for example.

Figure 5D:
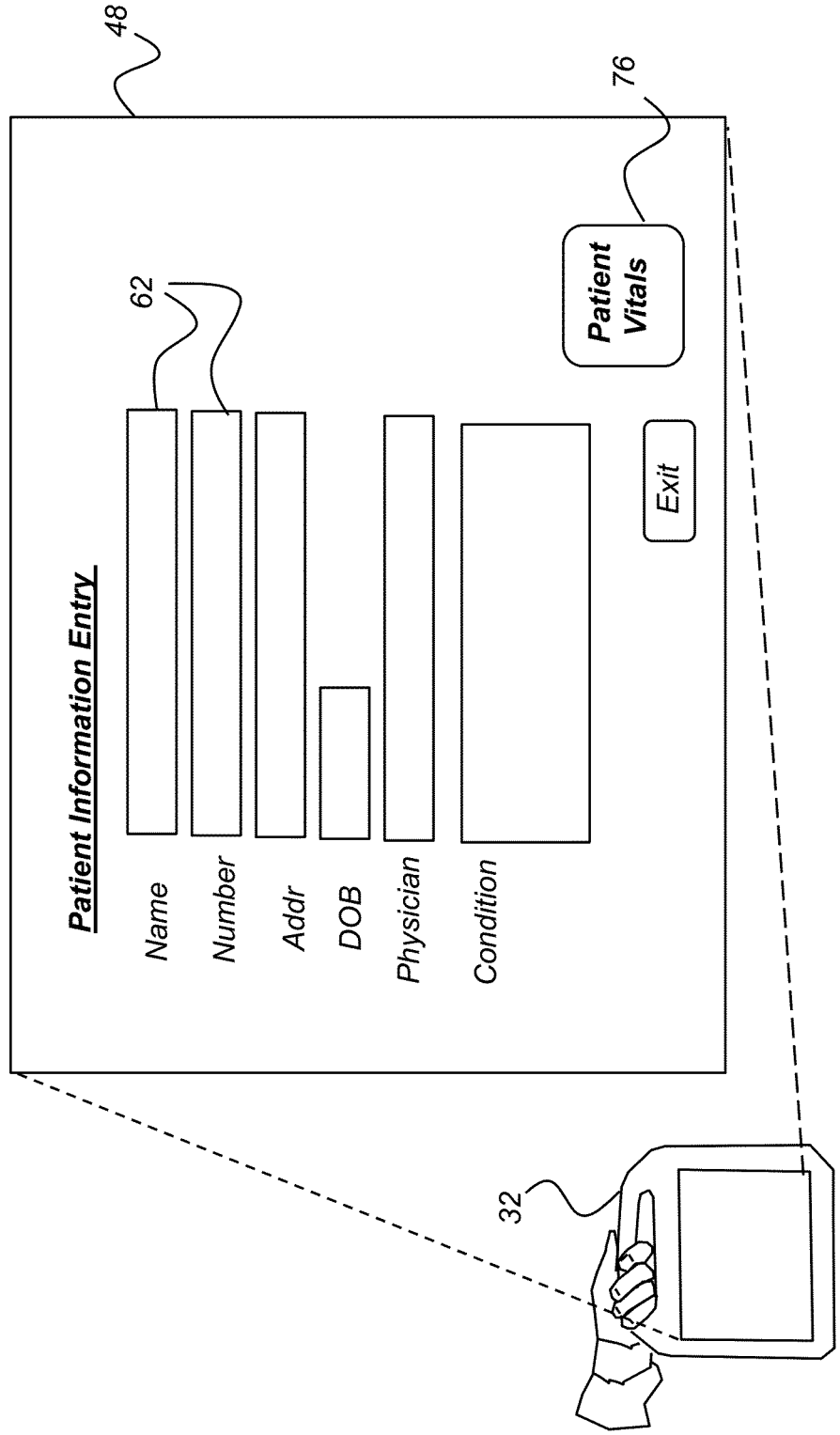
FIG. 5D is a plan view showing a mode of operation for entering patient information by the technologist or other personnel.

The plan view of FIG. 5D shows an exemplary entry screen for patient information and update, available on display interface unit 32. A keyboard, keypad, or other set of controls, as described previously, enable entry and update of patient information in one or more data fields 62. In one embodiment, audible entries are recorded for voice-actuated data entry and entered data are displayed in the indicated fields 62. The displayed information, downloaded from the hospital information system, HIS 20 in FIG. 1, can then be uploaded following editing, to keep the patient database current. Data entered can include various inputs to a structured report, for example. Patient vital information can be accessed at a control 76, such as by being downloaded from a networked HIS database, for example. In one embodiment, entry of the patient Name or Number fields automatically populates other information fields fir verification by the entering user. This occurs, for example, once the patient records can be uniquely identified from the user's data entry. For example, the entry of a unique Social Security number is sufficient for prompting a search of medical data and image databases in order to obtain information about the patient and, optionally, to ascertain whether or not other relevant diagnostic images are stored for that patient.

Figure 5E:
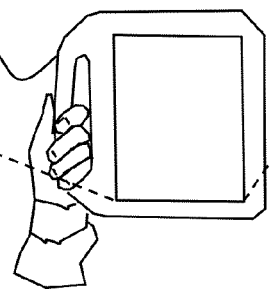
FIG. 5E is a plan view showing a mode of operation for entering medical information for a patient using the display interface unit.

FIG. 5E shows a checklist 64 that can be used by an attending nurse or physician to provide useful clinical information relative to the condition of the patient, including pathology and treatment data. Information in this format is particularly well-suited for touchscreen entry.

Figure 5F:
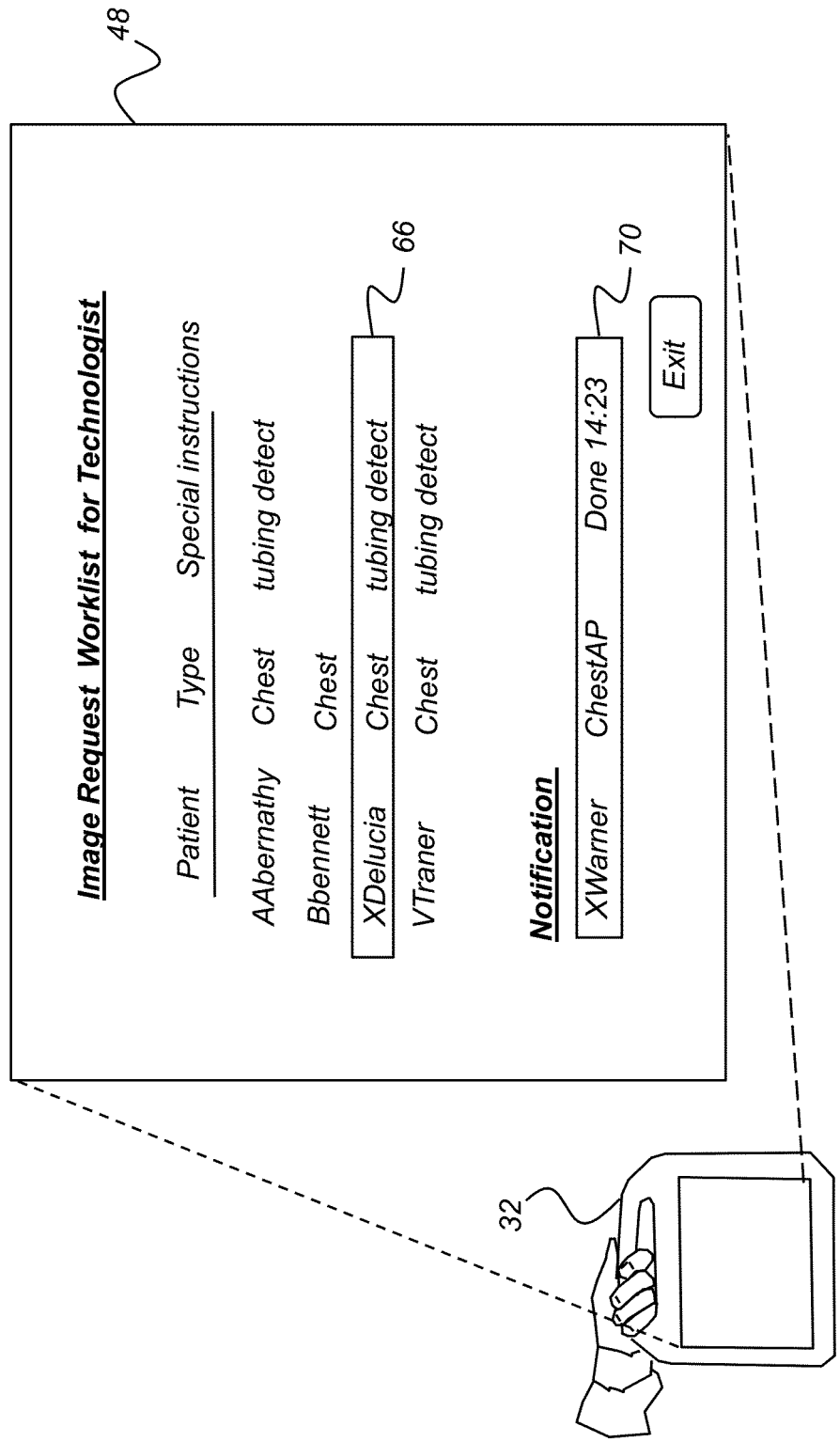
FIG. 5F is a plan view showing a mode of operation for displaying a technologist worklist for obtaining images.

FIG. 5F shows a mode of operation for displaying a technologist worklist for obtaining images. The worklist can include a priority indicator 66, such as a highlighting using color or text on a reversed background or using a blinking entry, for example. Optional priority indicator 66 can be used to direct the attention of the technologist to critical images that have priority over others. A notification 70 can also he provided as part of the worklist, or as a separate signal or message appearing on any of the display screens, indicating when image data has been obtained and the image is available for viewing. In one embodiment, a notification signal is provided for each image obtained. In an alternate embodiment, priority settings assigned to the image determine how notification is provided. Notification 70 may also indicate a potential problem detected by an automated diagnostic process that operates on the obtained image data and may indicate the need for radiologist review, for example. A beeping or other audible prompt may also be provided to indicate that a requested image has been obtained and is ready for viewing.

Figure 5G:
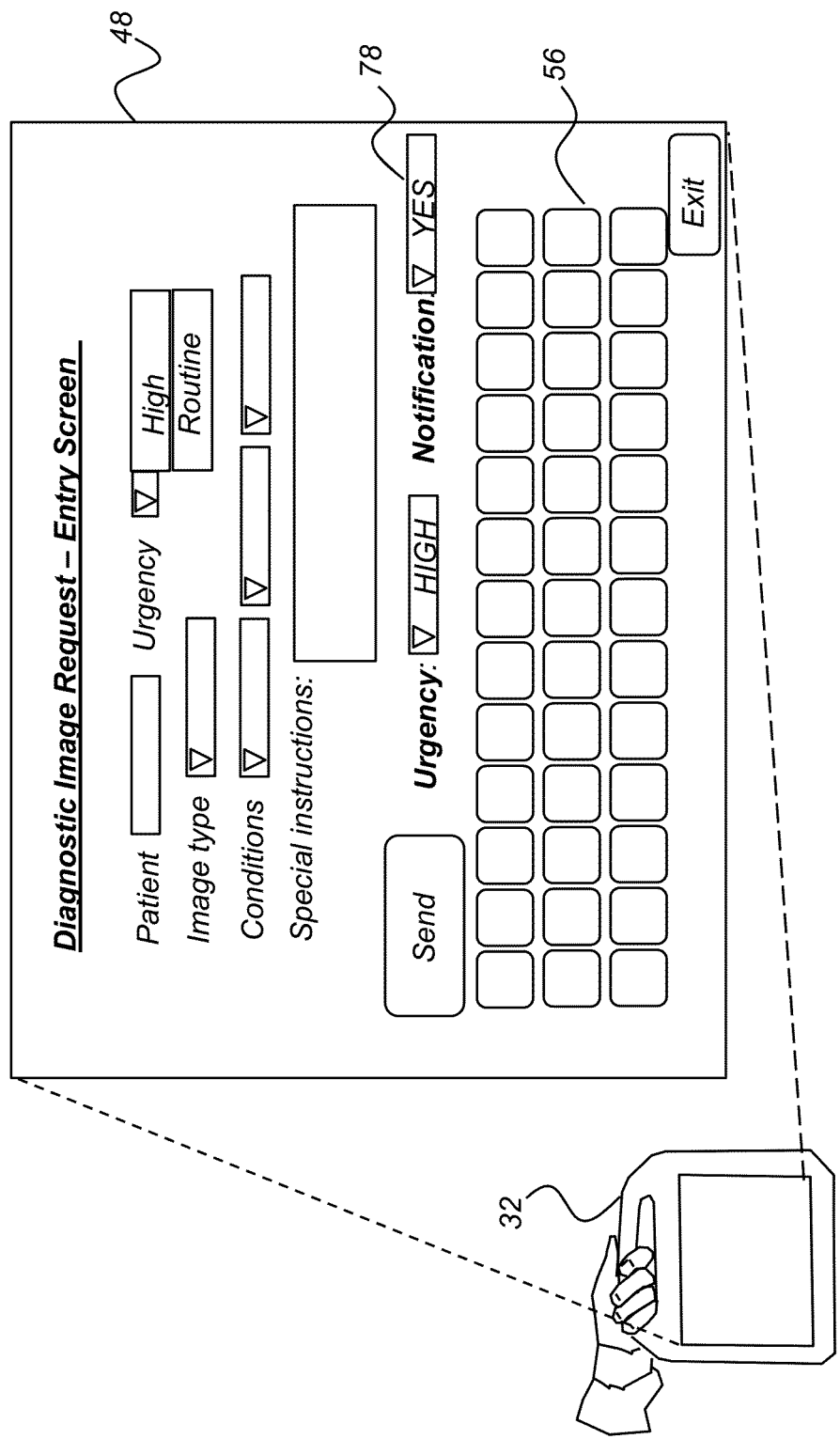
FIG. 5G is a plan view showing a mode of operation for entering a request for imaging from the mobile DR system.

FIG. 5G shows an operating mode in which display interface unit 32 obtains and processes a request for one or more diagnostic images or for additional services, such as laboratory tests or procedures, for example. The attending physician can use this as a convenient means for entering worklist items, for example, or for indicating the priority of pending imaging tasks. In the embodiment of FIG. 5G, on-board keypad 56 is provided for obtaining authorized entries. Optional controls 78 are provided to indicate a selected urgency level and to indicate what type of notification might be needed.

Figure 5H:
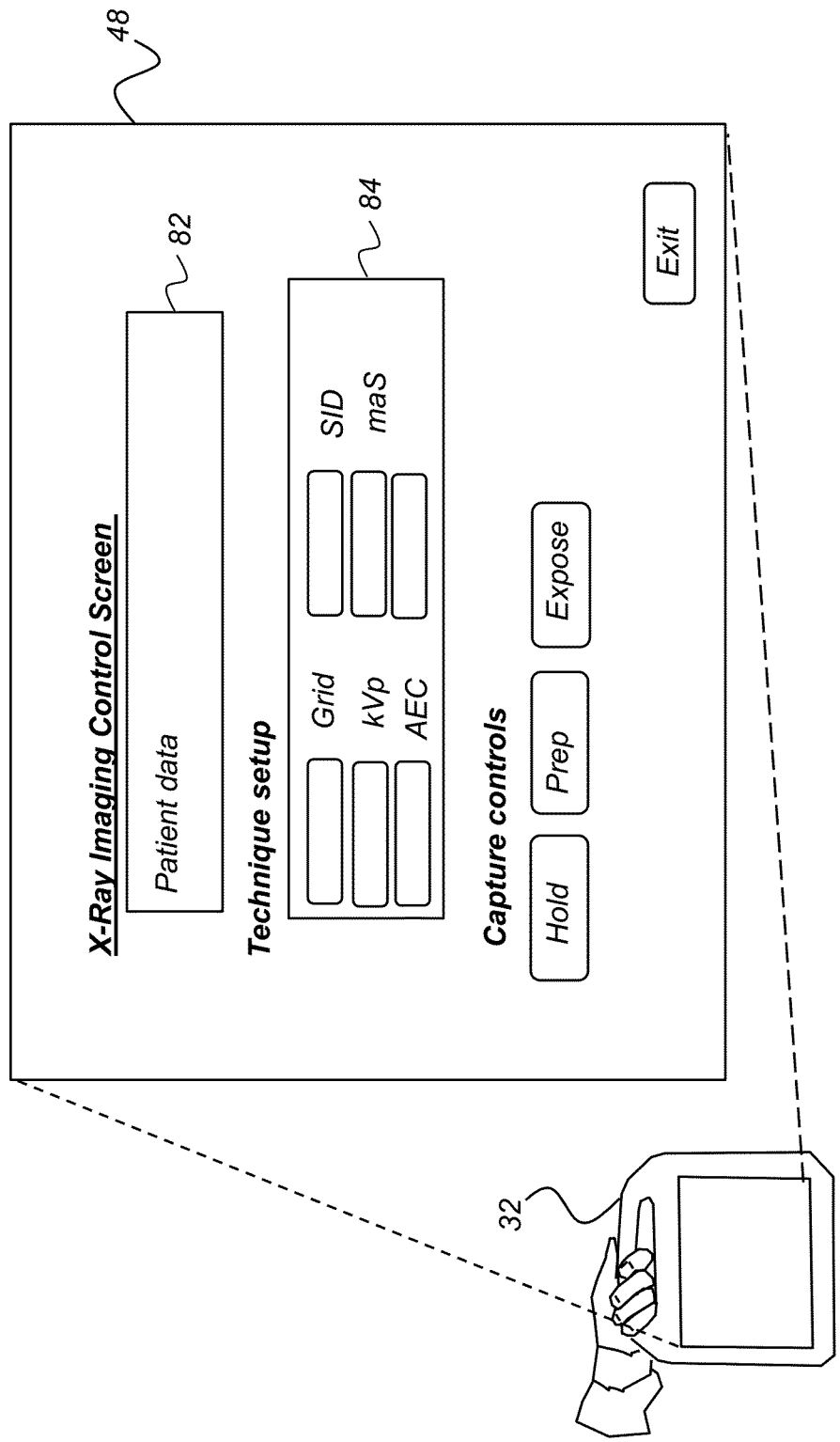
FIG. 5H is a plan view showing a mode of operation for displaying controls and parameter entry for the imaging process.

FIG. 5H shows a mode of operation in which display interface unit 32 serves as an operator console in which one or more controls for the image capture process itself arc displayed. In this mode, the technologist uses display interface unit 32 as a control panel for entering instructions that initiate imaging functions, with various controls that set up exposure variables (technique setup) in a technique setup entry area 84. A patient data display area 82 displays information for the identified patient for whom the image is to be obtained. Image capture controls required for receiver preparation and exposure are also provided on this display screen in one embodiment.

FIG. 5I shows a display of currently stored images and corresponding technique data for an identified patient. This display facilitates comparison of images and data from different systems. On this type of display screen, a smaller-scale image 60 displays, with corresponding technique data 72 also shown. The technique data is obtained from a medical database that links to images stored in the PACS archive in one embodiment. The viewer can use tabs or touch-based panning and dragging to select and position each of the stored images and view its technique data 72. A control 74 is provided that allows application of the active or displayed technique values for an upcoming image. This selection populates the screen of FIG. 5H, for example, providing the stored values as defaults or as starting-points for technique value entry. The technique data can include annotation that indicates how well a particular set of technique values worked and recommendations for adjustment according to various factors.

Figure 5J:
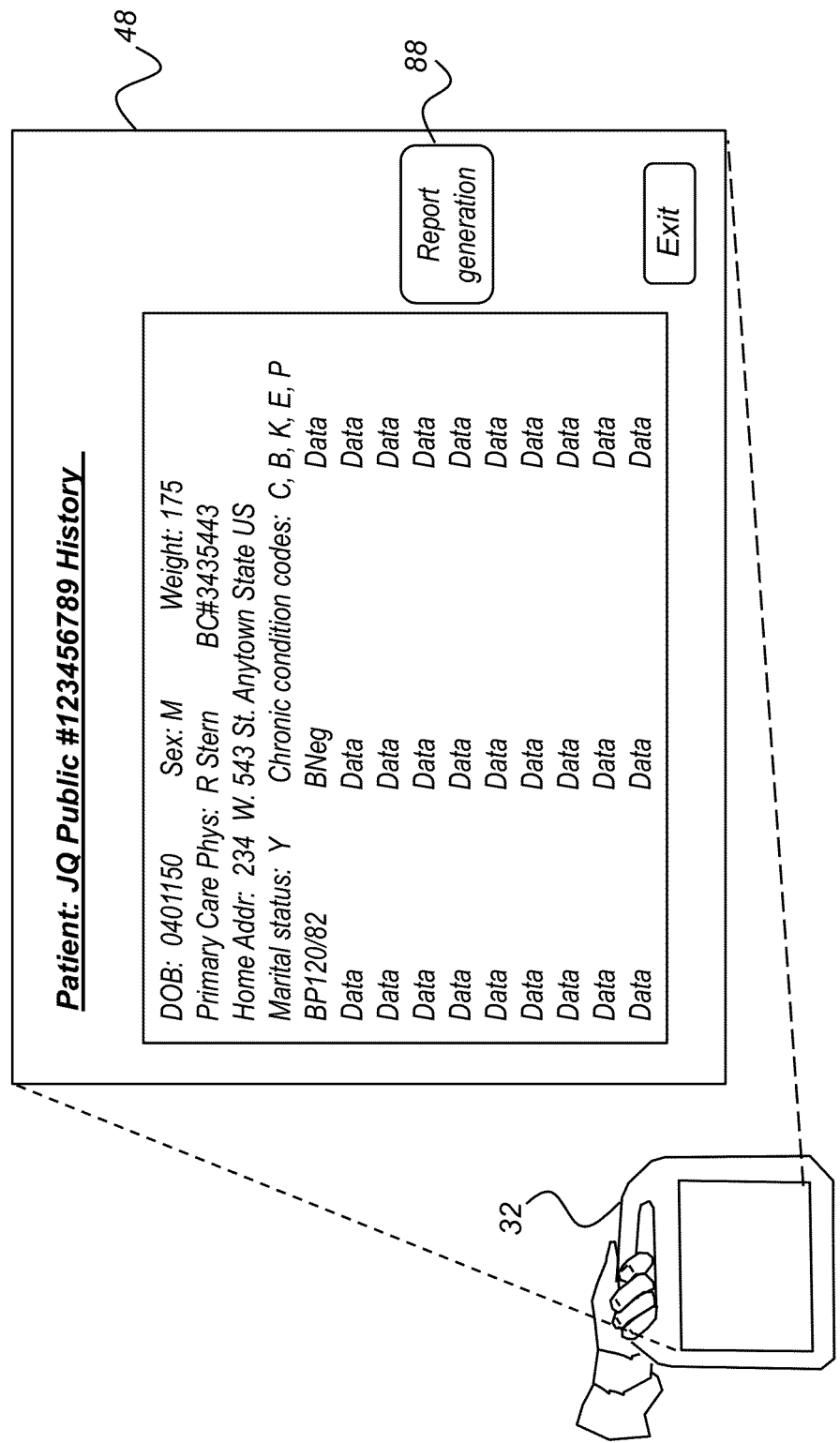
FIG. 5J is a plan view showing a mode of operation for displaying patient history.

FIG. 5J shows patient data obtained from a medical database and available for access by the attending physician or other authorized ICU personnel. Various data from the patient history can be displayed. A report generation button 88 enables the user to generate a structured report for current or historical patient images and related data, including use of data entered on any of the interface screens of FIGS. 5A-5J, for example. Voice actuation can also he used to provide input information for a structured report.

As can he seen from the example functions described with reference to FIGS. 5A through 5J, there can be a considerable body of image processing software and patient image data that are available at various networked processors. The apparatus and methods of the present invention make this information and capability more readily available and useful for meeting the needs of attending staff in ICU and related environments, where lower-resolution display may he sufficient for clinical assessment and urgent-care treatment. The apparatus and methods of the present invention work with patient image data that may also he examined by a radiologist at a later time, but provides this image data in a format that is more readily usable to ICU treatment staff.

Figure 6:
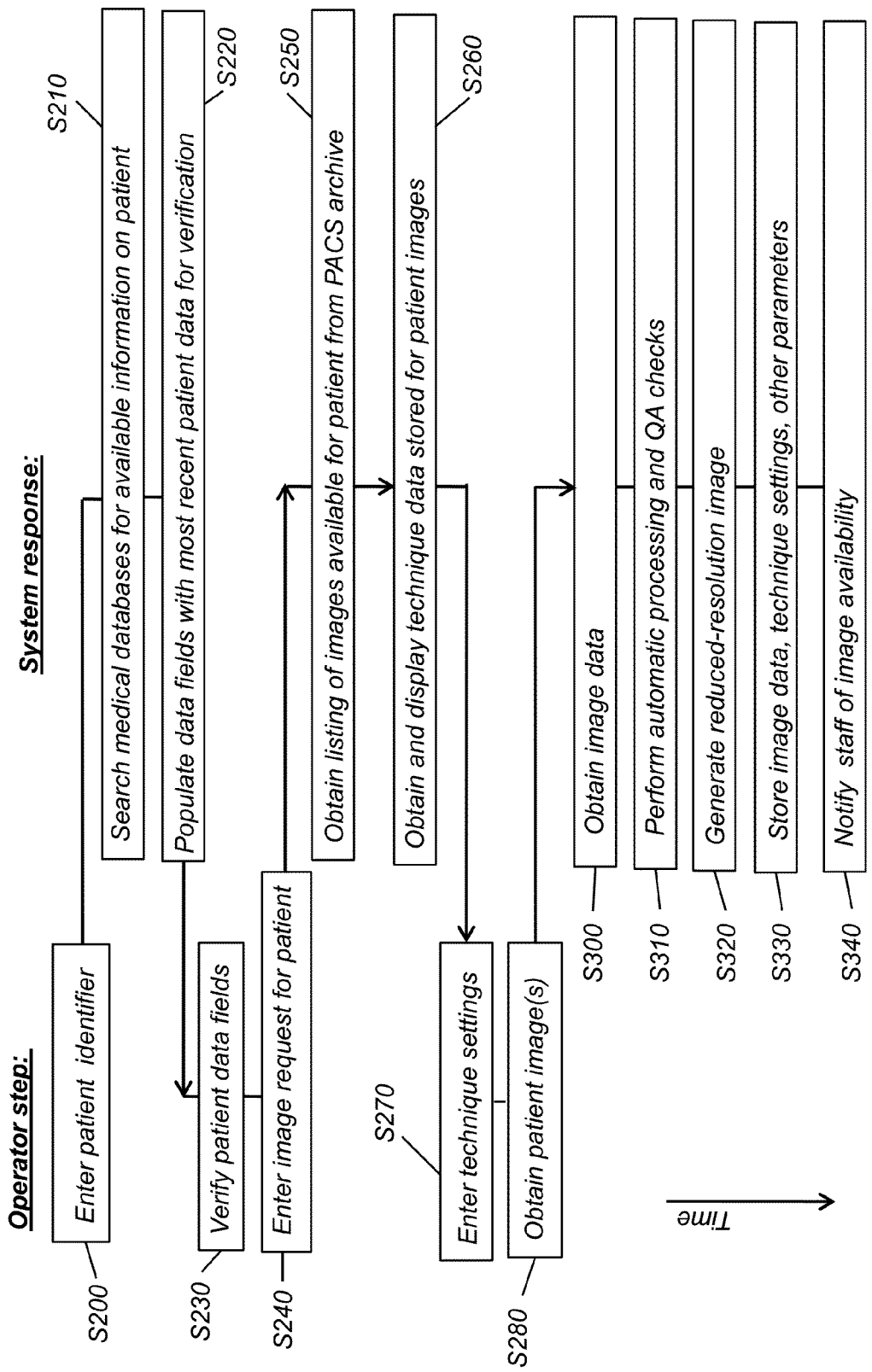
FIG. 6 is a logic flow diagram showing the sequence of operator steps and system responses for obtaining patient images according to one embodiment.

The logic flow diagram of FIG. 6 shows how image processing workstation 30 interacts with the technologist or other user and obtains information to support more efficient workflow and more effective treatment for ICU patients. Operator steps are in the column at the left; system responses are shown to the right. In a patient identifier entry step S200, the operator or technologist enters identifying patient information, such as on the interface screen shown in FIG. 5D. In response to step S200, a database search step S210 is executed, in which various HIS and other medical databases are accessed and searched for obtaining any useful information about the patient. A data field population step S220 then populates data fields in the interface screen of FIG. 5D and elsewhere, such as in FIG. 5E for example, with historical or default patient data. Included in step S220 is information related to techniques used for obtaining other diagnostic images for the patient.

A verification step S230 accepts operator verification of patient identification information, allowing the operator or technologist to edit or re-enter any applicable information fields with suitable data for the patient. In an image request entry step S240, the clinical staff requests an image for the patient or requests additional services for the patient, such as using the interface screen of FIG. 5G. An image listing step S250 then obtains a listing of patient images that are available from PACS and other diagnostic image archival systems. These images can then be optionally downloaded for comparison against current images, as described previously with respect to FIGS. 5B and 5I. A technique data display step S260 obtains and displays technique data stored with the archived images, optionally populating data fields in technique setup, such as that shown in FIG. 5H. In a technique settings entry step S270, the technologist enters and edits the pre-populated data fields prior to image capture.

An obtain images step S280 is executed, in which the x-ray image is obtained, such as by technologist entry of commands from the screen of FIG. 5H. An obtain image data step S300 follows, during which the exposure occurs and diagnostic image data is formed and downloaded from the DR detector, as described earlier with reference to FIGS. 1 and 2.

Once the digital radiography image is obtained, a perform automatic processing step S310 is executed on the data, with presentation of processing results on the display. Automatic processing can include, for example, presetting visualization settings for life support line visualizations, as described earlier with reference to the interface screen of FIG. 5C. Automatic processing can also include adjusting variables for brightness, contrast, and sharpness of images or variables for enhancing the patient's pneumothorax, for example. Automatic processing can include features for computer assisted diagnosis, such as catheter placements. In addition, results of automatic quality assurance can be displayed on the interface screen of FIG. 5A, for example, and can include data from algorithms that check patient positioning, motion, exposure relative to an aim, clipped anatomy, contrast, and other variables and attributes of interest.

A generate reduced-resolution image step S320 then performs the resolution scaling of the image data in order to display the image on the lower-resolution screen of display interface unit 32, such as shown in screens of FIGS. 5A, 5B, 5C, and 5I, for example. A storage step S330 follows, in which image data, technique settings, and other data about the patient and related imaging parameters are stored for later access. An optional notification step S340 then informs members of the patient care staff that the needed image has been obtained and is available for clinical as well as diagnostic purposes.

Automated Processing

As noted previously, perform automatic processing step S310 in FIG. 6 includes evaluation of image data for clinical information as well as for image quality and overall diagnostic suitability. Embodiments of the present invention expand upon these aspects of automated image processing and analysis and provide ways to report this information and to use evaluation results to further help the technician and the clinical staff to respond to detected patient conditions and to image quality and suitability problems.

In the context of the present disclosure, "image suitability" or "diagnostic suitability" relates to the usability and status of an obtained image for use as a diagnostic tool. A number of diagnostic suitability criteria relate to image quality as obtained using the current set of techniques. Low contrast, for example, relates to poor image quality and may be due to over- or under-exposure, inappropriate grid use, or other technique-related factor. It can be appreciated that low contrast can have a negative impact on the diagnostic suitability of an image. Other diagnostic suitability criteria relate to imaging conditions that may or may not he within control of the technician and may or may not affect whether or not the image can be used effectively for diagnosis. Patient motion is one diagnostic suitability criteria that lies outside of direct technician control; however, this condition should be flagged to the technician if detected. Grid cutoff, anatomy cutoff, and missing marker conditions may or may not he acceptable in a given case, depending on patient condition, portions of the patient being imaged, and other factors.

Figure 7:
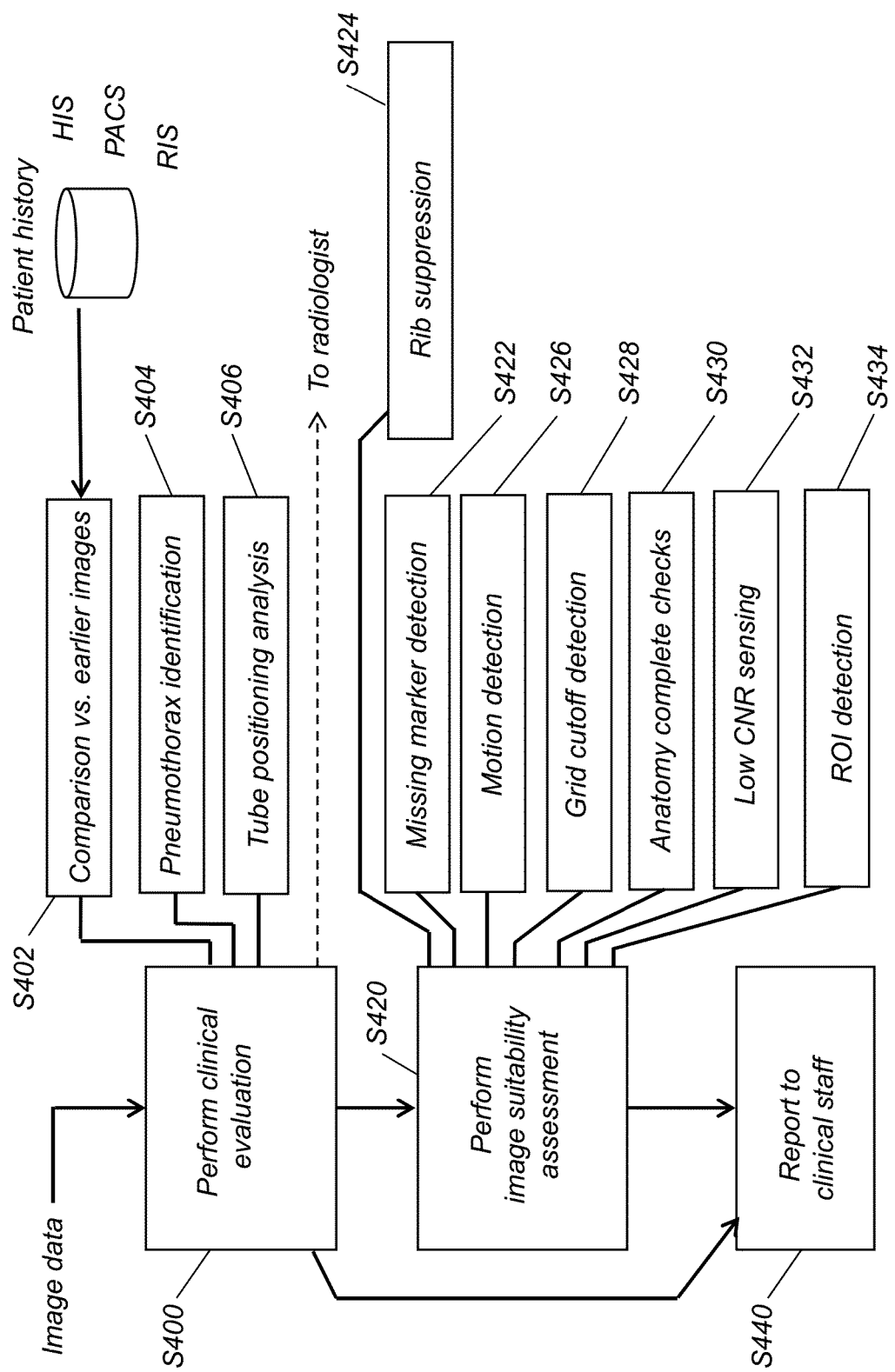
FIG. 7 is a logic flow diagram that shows an automated processing sequence for evaluating diagnostic suitability and clinical information from the obtained image.

Referring to the logic flow diagram of FIG. 7, some portions of the automatic processing sequence are shown by way of example. The received image data is first processed in an initial clinical evaluation step S400 that performs image processing to check for indications of the clinical condition of the patient. Of particular interest for mobile radiology and ICU applications is information that is particularly timely and relevant to urgent patient treatment. Exemplary sub-steps for clinical evaluation include a comparison step S402 in which the newly obtained image is compared against previous images for the same patient. This comparison may relate to the overall image or to a portion or region of interest in an image. A pneumothorax identification step S404 also executes to detect and report a pneumothorax condition. A tube position analysis step S406 checks to identify tube and tip positioning in the obtained image. Following execution of clinical evaluation step S400 and any of its related sub-steps, results can he provided to a radiologist as well as being reported to clinical staff in the treatment facility.

Continuing with the logic flow diagram of FIG. 7, an image suitability assessment step S420 is also executed. This step processes the image using a set of predefined criteria for diagnostic suitability of the image, using any of a number of image analysis utilities that check various aspects of the image in order to verify that the image itself is usable for diagnosis. Related sub-steps for image suitability assessment include a marker detection step S422 that checks for a missing marker in the image content. A rib suppression step S424 applies image processing to reduce rib content from chest-x-ray images. Rib suppression is described, for example in U.S. patent application publication No. 2009/0214099 entitled "Method of Suppressing Obscuring Features in an Image" by Merlet. A motion detection step S426 checks image content to detect excessive motion that may justify obtaining another exposure. Motion detection within an x-ray image is described, for example, in U.S. patent application publication No. 2009/0274272 entitled "Methods and Apparatus for Obtaining Low-Dose Imaging" by Martin et al. A grid cutoff detection step S428 analyzes the input data to detect grid cutoff effects. An anatomy complete checks step S430 determines whether or not there is missing anatomy, such as clipped anatomy, in the obtained image data. Among methods usable for anatomy complete checks step S430 are those described in commonly assigned U.S. patent application publication No. 2009/0041325 entitled "Method for Detecting Clipped Anatomy in Medical Images" by Hui Luo. A low contrast detection step S432 senses a low contrast condition, detected using any of a number of techniques and metrics known to those skilled in the image analysis arts. An ROI detection step S434 determines if the region of interest lies within the obtained image and may provide boundary data for the region of interest. It must be noted that the criteria shown and described with reference to FIG. 7 are exemplary and other predefined criteria for diagnostic suitability of the image could alternately be used.

Results from processes associated with clinical evaluation step S400 and with image suitability assessment step S420 are then provided to the clinical staff in a reporting step S440. These results can be presented to the technician on display interface unit 32 along with other useful information, as described in more detail subsequently.

Figure 8:
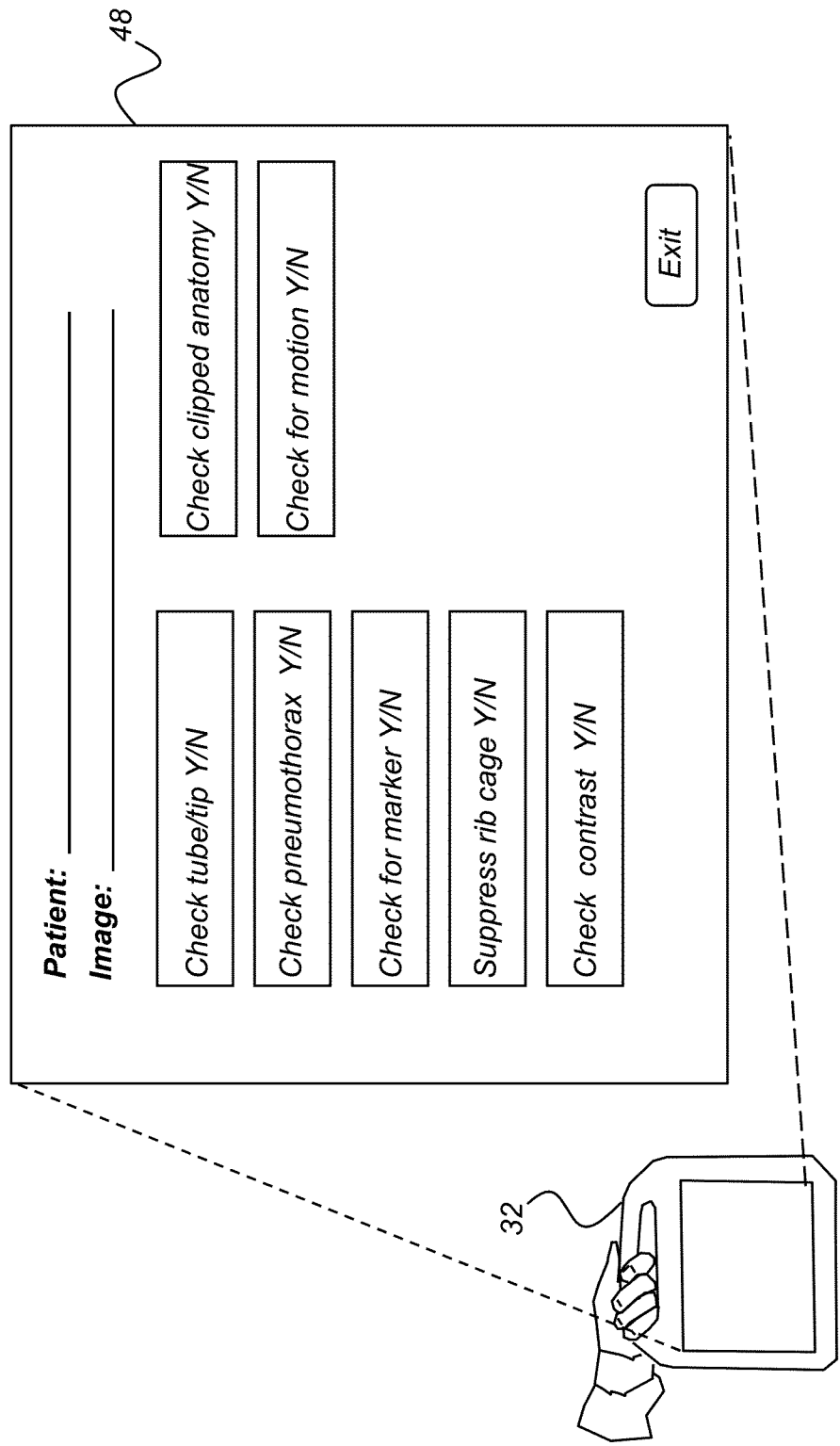
FIG. 8 is a plan view showing a mode of operation for displaying selectable processes for analyzing the clinical condition of the patient and diagnostic suitability of the obtained image.

In addition to automatic processing of the image data for clinical evaluation and image suitability, as described with reference to the logic flow diagram of FIG. 7, explicit instructions can be entered to execute this processing or, alternately, to disable one or more automated functions. FIG. 8 shows an operating mode in which the technician or other operator can request processing of a selected image. This capability can alternately be used to enable or disable specific processing checks for automated image processing.

Figure 9:
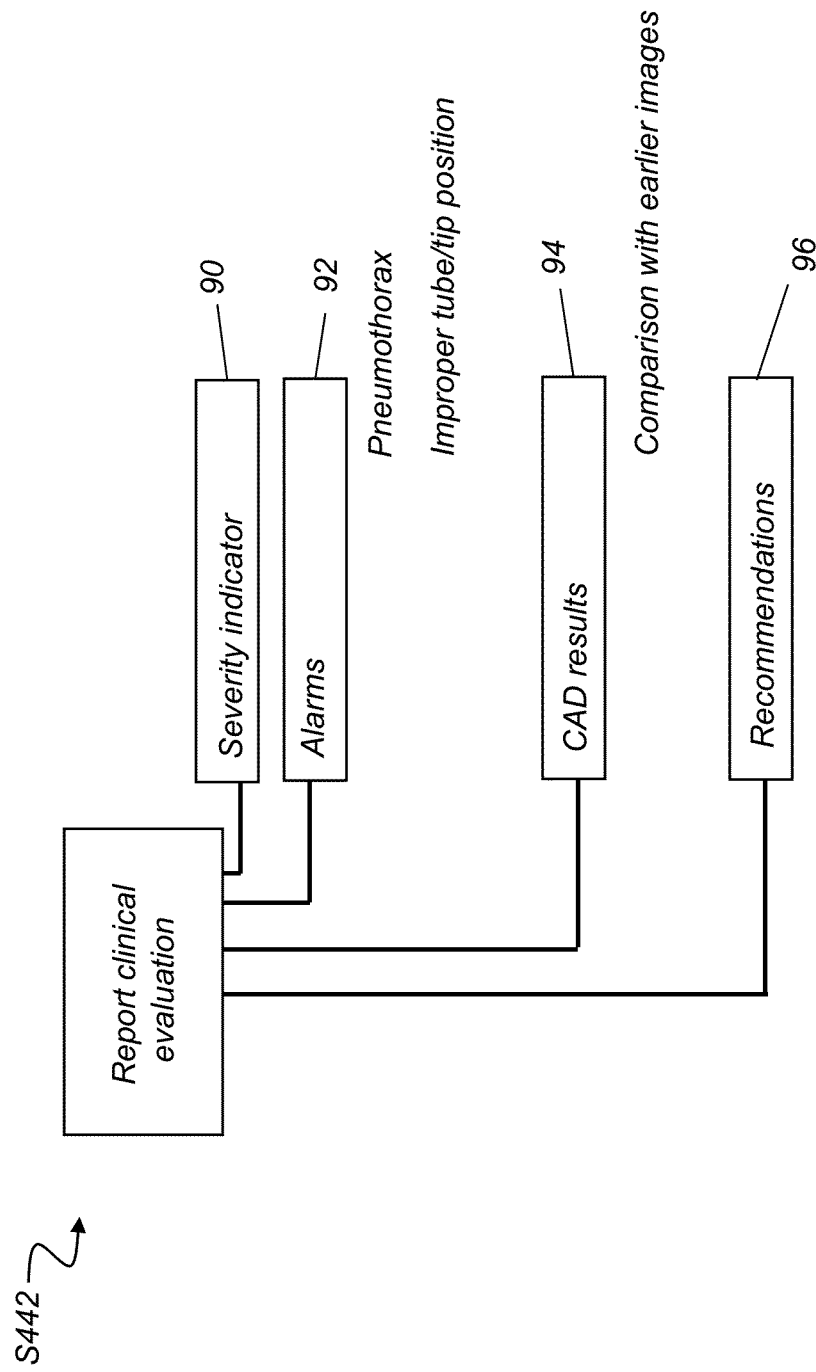
FIG. 9 is a logic flow diagram showing steps for reporting clinical information about the patient.

Reporting the results of processes associated with clinical evaluation step S400 and with image suitability assessment step S420 is done as part of reporting step S440. The logic flow diagram of FIG. 9 shows procedures used in a clinical evaluation reporting step S442. For processing results that indicate a severe condition or one that can be of particular relevance to care and treatment of the patient, a severity indicator 90 is provided. This can be a message displayed on interface 32 for less serious conditions. Severity can alternately he indicated to the technician at display interface 32, for example, by an alarm 92 using an audible lone or beep, highlighting or flashing a display element, or in some other suitable manner. Other CAD results 94 can be provided to the technician or other operator, reported as part of the patient information (FIGS. 5D or 5J), for example. Recommendations 96 can be provided to the operator for improving the image data or correcting detected problems, as described subsequently.

Figure 10:
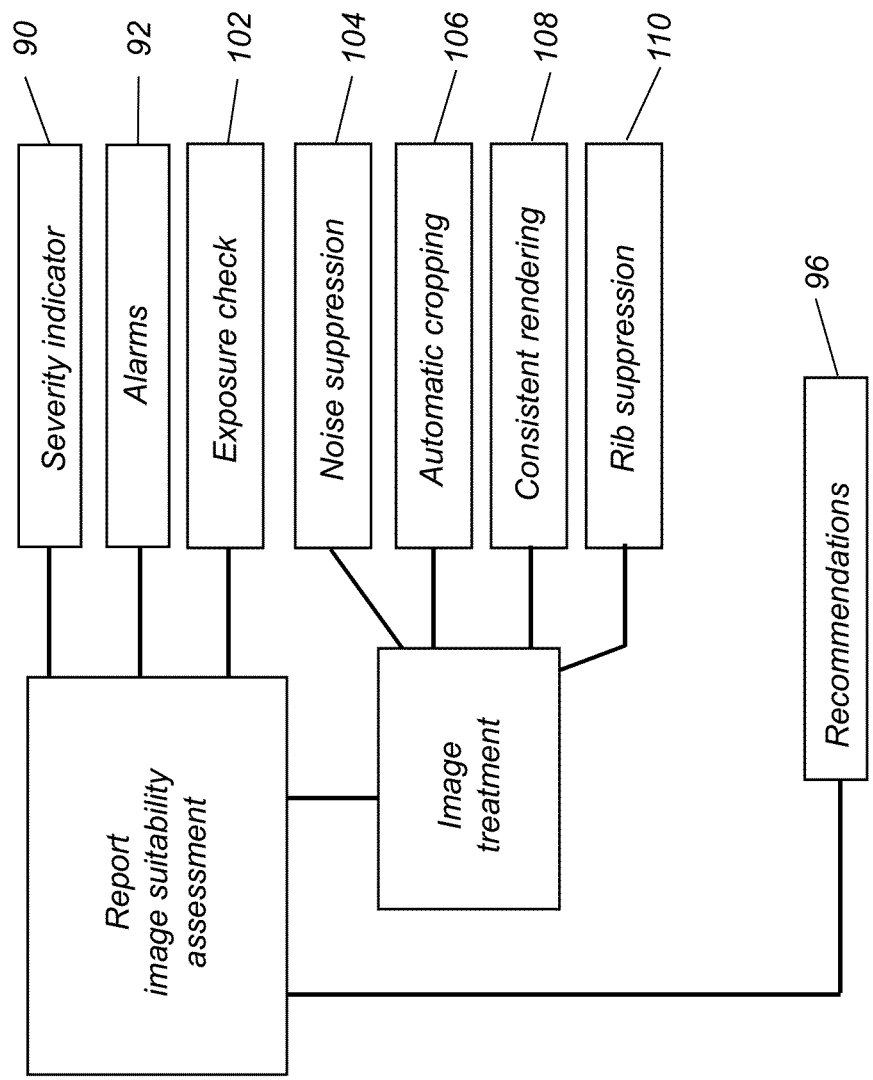
FIG. 10 is a logic flow diagram showing steps for reporting image suitability.

Reporting the results of processes associated with image suitability assessment step S420 (FIG. 7) is also done as part of reporting step S440. The logic flow diagram of FIG. 10 shows procedures used in an image suitability reporting step S444. For processing results that indicate a problem that impacts diagnostic image suitability, a severity indicator 90 is provided. This can be a message displayed on interface 32 for less serious imaging problems. Severity can alternately be indicated to the technician at display interface 32, for example, by an alarm 92 using an audible tone or beep, highlighting or flashing a display element, or in sonic other suitable manner. With this capability, problems such as detected motion, clipped anatomy, missing marker, or poor contrast can be reported quickly to the technician, enabling rapid response. An exposure check 102 evaluates the contrast obtained based on the exposure settings used and other values and determines whether or not exposure settings used are appropriate for the image obtained: There are also a number of image treatment processes that are executed. Noise suppression 104 applies noise suppression processing to the obtained image. Automatic cropping 106 performs any necessary cropping of the image. Consistent rendering 108 helps to adjust image intensity levels to a suitable range for rendering. Rib suppression 110 then performs algorithms for suppressing these structures in the data for a chest x-ray.

Figure 11:
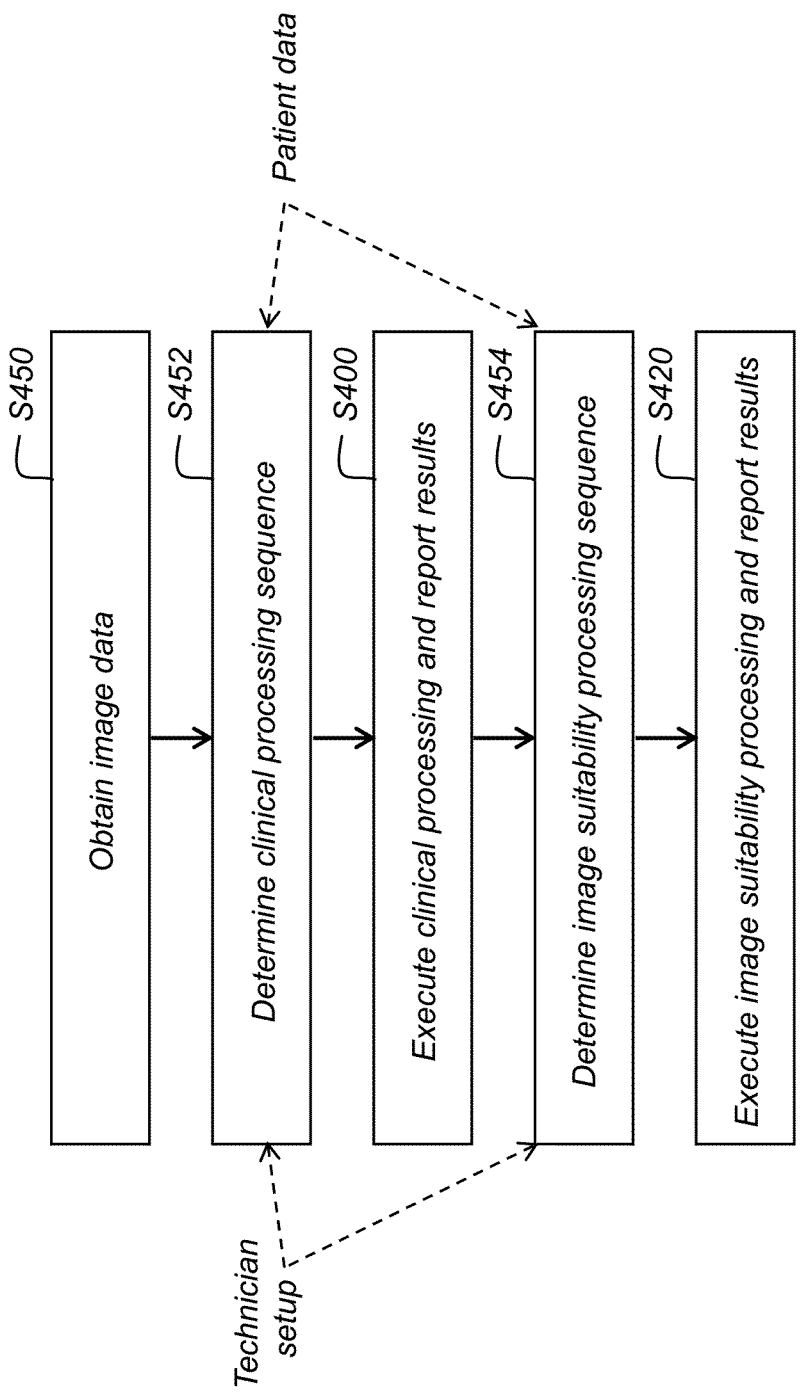
FIG. 11 is a logic flow diagram that shows a sequence of operations for processing image data and assessing image diagnostic suitability.

The processing sequence that is followed can be based on various factors, such as variables entered by the technician or doctor and information about the patient and patient condition. The logic flow diagram of FIG. 11 shows the basic sequence of operations that are used for processing image data according to one embodiment. Image data is received in an obtain image data step S450. A determine clinical processing step S452 then determines what processes are executed as part of perform clinical evaluation step S400 in FIG. 7. For example, the processing used can vary according to the type of x-ray that has been obtained and factors such as the patient's age or sex, and other variables. In addition, operator setup can enable or disable various processing steps, as was described earlier with reference to FIG. 8. Clinical evaluation step S400 can then he executed, as was described with reference to FIG. 7. A determine image suitability processing sequence step S454 is then executed, determining what processes are executed as part of image suitability assessment step S420 in FIG. 7. Again, the type of processing used can vary according to type of x-ray that has been obtained and other variables. Image suitability assessment step S420 can then be executed, as was described with reference to FIG. 7.

Figure 12:
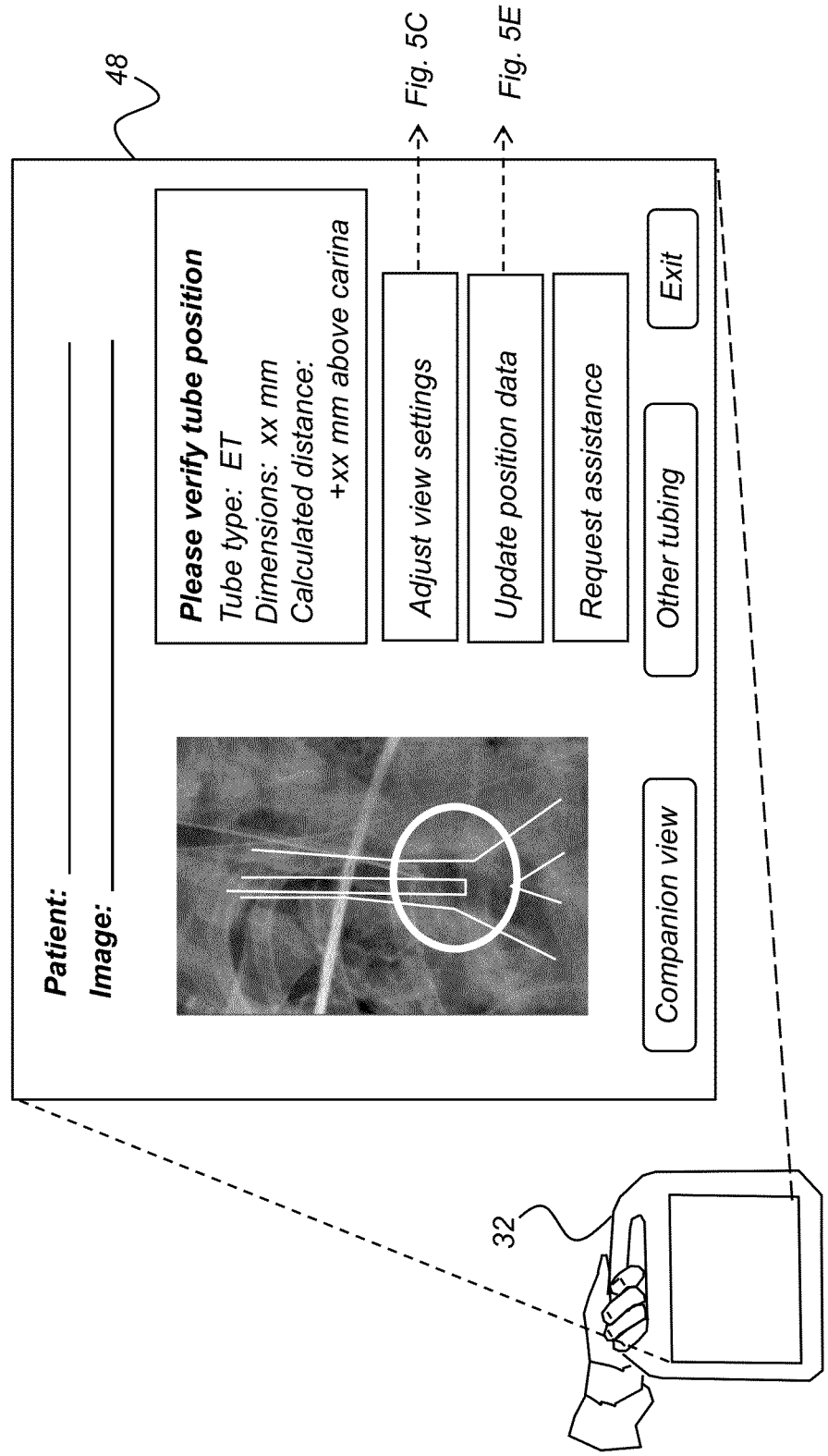
FIG. 12 is a plan view showing a mode of operation for displaying recommended corrective actions for a detected result related to diagnostic suitability.

Both clinical evaluation reporting step S442 in FIG. 9 and image suitability reporting step S444 in FIG. 10 include recommendations 96 that are transmitted hack to the technician or operator or other user of the mobile radiography apparatus. Referring to the exemplary display shown in FIG. 12, recommendations for a condition of clinical concern can include information about the detected problem, such as tube type and placement detection as shown. Utilities for adjusting display settings and updating status information are also provided, so that the operator can deal with the detected problem, whether by correcting the problem, by retaking the image under changed conditions, or by reporting the problem to appropriate staff for corrective action. In the tube position recommendations example shown in FIG. 12, analysis software has detected a likely tube positioning problem. This problem is presented to the operator using a text message as well as by highlighting the area of the image over which the problem has been detected. Because the technician may not be the appropriate staff member to correct the problem in some cases, utilities are provided for reporting the problem to others and requesting assistance. Where multiple tubing elements are detected, as in the example of FIG. 12, the display enables the viewer to check other tubing for proper positioning. Capability for a companion view, with particular image enhancement for tubing and tip placement, is also provided.

Figure 13:
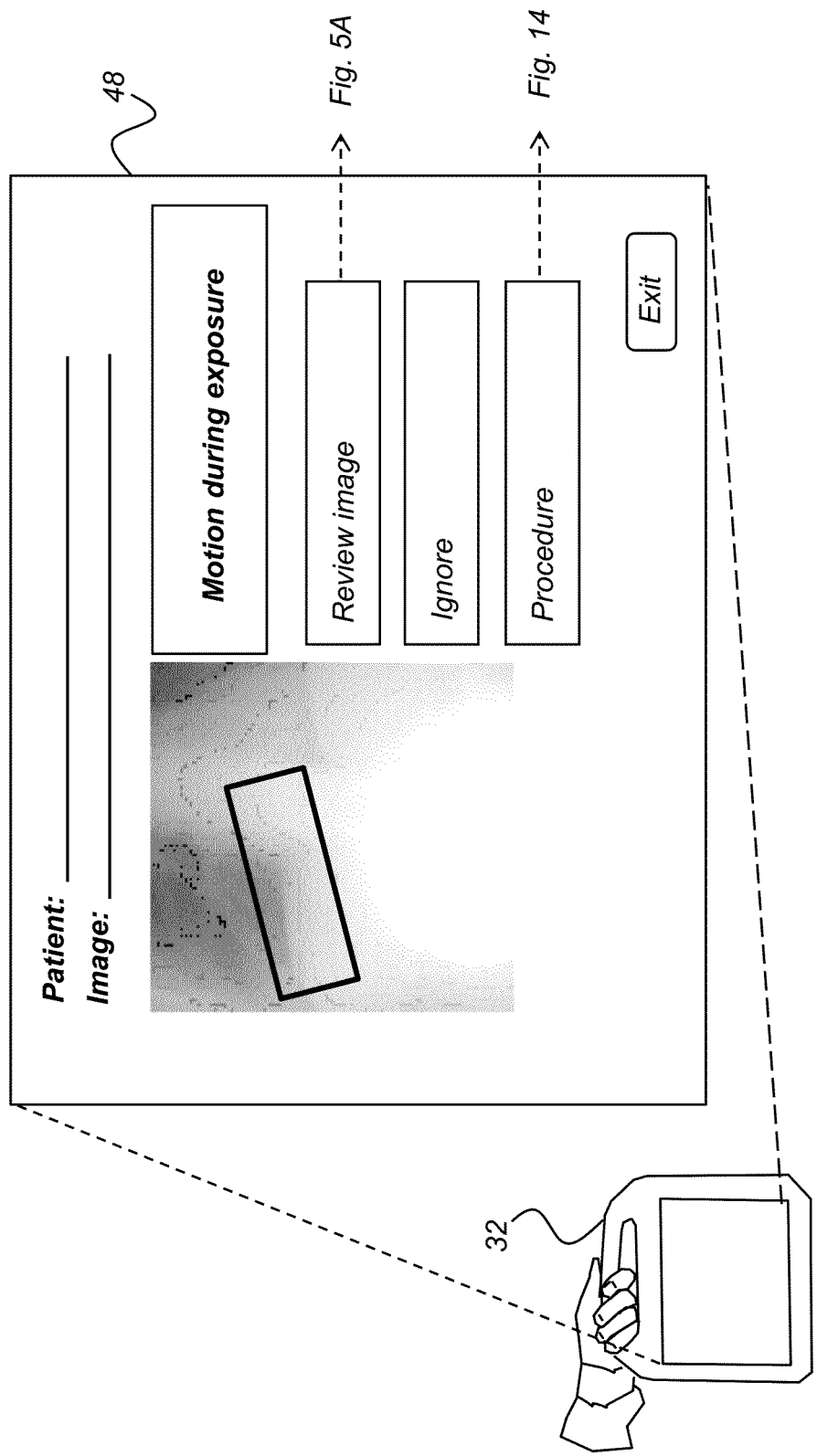
FIG. 13 is a plan view showing a mode of operation for displaying motion detection in one embodiment.

Problems with image suitability can often he corrected by the technician with execution of a few routine steps. The display shown in FIG. 13 gives an example in which motion is detected and shows a set of operator options for problem resolution. An initial step is image review, in order for the technician to ascertain whether or not a detected problem is perceptible and could jeopardize accurate diagnosis. The technician can ignore the detected problem or may opt to correct the problem and re-take the image. As FIG. 13 shows, one or more areas of the image over which a problem is detected may he highlighted on operator interface display 48. Utilities for image review, such as zoom and crop tools for example, may also be linked to the recommendations display.

Figure 14:
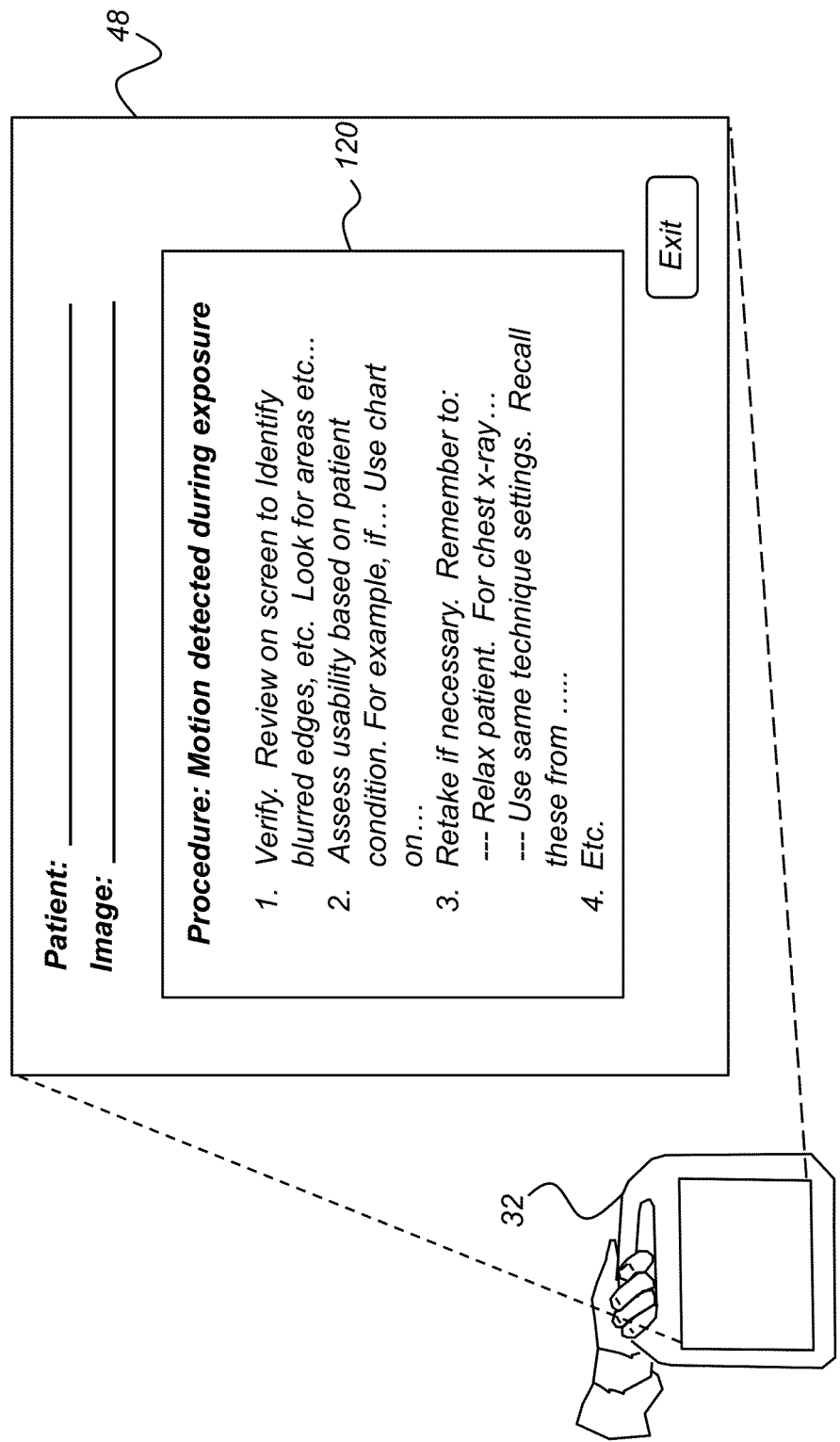
FIG. 14 is a plan view showing a mode of operation for displaying a listing of corrective actions.

Embodiments of the present invention also provide procedural information for correcting a problem related to a clinical condition or to image suitability. Referring to FIG. 14, accessible from the display of FIG. 13, operator interface display 48 also provides a listing 120 of one or more corrective actions or of a sequence of actions that can be applied for addressing the imaging problem. Listing 120 can he provided from standard operating procedures that are specific to the hospital or other care facility or may be default procedures from standardized content provided by the system integrator or manufacturer. For example, a standard set of procedures can be applied to determine whether the image includes the full anatomy or there is a clipped-anatomy condition, and how to correct for this condition. Procedures are listed in order of likelihood for reducing or minimizing the detected problem. The procedural listing may include suggestions or recommendations, such as for grid use and technique adjustments. In one embodiment, CAD software analyzes an image suitability problem with reference to known settings and orders or reorders the procedural listing accordingly.

A standard set of utilities can he provided for linking to online text or other stored information that contains the required procedures. In one embodiment, an online operation manual for imaging using mobile digital radiography system 100 is maintained under administrative and supervisory control. Useful portions of the on-line documentation are made available to the technician in response to the types of images obtained, patient condition information and image suitability problems detected by the system. In this way, not only are various problems with regard to patient condition and image suitability detected and reported, but remedial steps and suggestions for their correction are made readily available to the technician and attending staff.

In its various aspects, the method of the present invention executes on a host processor. As used herein, the term "host processor" encompasses any of a number of possible configurations of logic processing hardware and network configurations and may include one or more computers, computer workstations, embedded computers and processors, and microprocessors for example. Referring back to FIG. 2, the host processor is computer 42 that is part of mobile digital radiography system 100 in one embodiment. In an alternate networked embodiment, as shown previously in FIG. 1, image processing workstation 30 also provides some host processor functions, so that the networked combination of computer 42 in the mobile system and image processing workstation 30 collectively provides a host processor, as the term is used in the context of the present disclosure. It can be appreciated by those skilled in the data processing arts that various processing functions can be distributed, executed at different computers and processors that cooperate over a network, collectively providing a host processor. This type of distributed host processor arrangement can be particularly useful, for example, where specific image processing functions are best suited for operation on specific computer systems or already operate on specific systems.

The control console of mobile digital radiography system 100 can be broadly interpreted as the operator interface device at which operator instructions for system operation are entered and includes a display of some type for feedback information from the system. In one embodiment, the control console is the portable display interface unit 32 that is detachable from the system; in an alternate embodiment, the function of the control console is distributed between display interface unit 32 and controls mounted on cart 40 (FIG. 2).

Embodiments of the present invention may have the form of computer-implemented processes and apparatus for practicing those processes. Embodiments of the invention may also he embodied in the form of computer program code containing instructions embodied in tangible media, such as magnetic storage media such as a hard drive or removable magnetic media, optical storage media such as CD-ROMs, or any other computer-readable storage medium, wherein, when the computer program code for the embodiment is loaded into and executed by a computer or other type of host processor, the computer or processor becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a suitable logic processor or computer, the computer becomes an apparatus for practicing the invention. When implemented on a dedicated microprocessor, the computer program code segments configure the microprocessor to create specific logic circuits for program logic execution. One or more encoded signals that are provided as output can he used to display an image or data, store data or operator instructions, or upload or download images and data from networked computer systems, for example.

The invention has been described in detail with particular reference to a presently preferred embodiment, but it will be understood that variations and modifications can be effected within the spirit and scope of the invention. For example, the methods and system of the present invention can be used with a mobile radiography system as well as with other portable and stationary imaging apparatus. The invention can be used with imaging systems that use exposure energy at a single energy level or at multiple energy levels. Embodiments of the present invention can help to improve imaging results for cone-beam computed tomography (CBCT) imaging systems that reconstruct 3-D volume image data from 2-D projection image content. User interface areas shown in figures of the present disclosure are exemplary and are provided to help illustrate various features of the present invention. Any number of alternate arrangements of user interface areas and user interaction utilities and interface traversal sequences can be used.

The presently disclosed embodiments are therefore considered in all respects to he illustrative and not restrictive. The scope of the invention is indicated by the appended claims, and all changes that come within the meaning and range of equivalents thereof are intended to be embraced therein.

The invention claimed is:

1. A method for processing a radiographic image of a patient, executed at least in part on a host processor, comprising:

initiating exposure in response to an instruction entered from an operator console;

obtaining radiographic image data from a digital detector that is subjected to the exposure;

using a computer processor, automatically analyzing the obtained radiographic image data according to a plurality of predefined criteria for diagnostic suitability of the radiographic image;

indicating one or more results of the diagnostic suitability analysis at the operator console, the one or more results including one or more problems with the diagnostic suitability; and automatically providing, at the operator console, a listing of one or more corrective actions based on the indicated one or more results.

2. The method of claim 1 further comprising reporting a clinical condition according to a predefined sequence of steps for clinical evaluation executed on the obtained image data.

3. The method of claim 1 wherein obtaining the radiographic image comprises obtaining the image at a mobile radiography system.

4. The method of claim 1 further comprising applying a rib suppression processing to the obtained radiographic image.

5. The method of claim 1 wherein the listing is from data obtained over a network connection.

6. The method of claim 1 wherein the plurality of predefined criteria for diagnostic suitability of the image relates to information about the patient.

7. The method of claim 1 wherein the plurality of predefined criteria for diagnostic suitability of the image relates to information from the technician.

8. The method of claim 1 wherein the corrective actions include re-taking the image.

9. The method of claim 1 wherein the predefined criteria for diagnostic suitability are specified by technician entry.

10. The method of claim 1 wherein indicating one or more results of the diagnostic suitability analysis comprises providing an audible indicator.

11. The method of claim 1 wherein indicating one or more results of the diagnostic suitability analysis comprises providing a displayed indicator.

12. The method of claim 1 wherein the listing is from data stored in a memory that is accessible to the operator console.

13. The method of claim 1 further comprising reporting a severity indicator indicative of the diagnostic image suitability.

14. The method of claim 13 further comprising reporting the severity indicator by at least one of the following: emitting an alarm, emitting an audible tone, displaying a highlighting of at least a portion of the radiographic image data on the operator console, transmitting a text message, and flashing a display element on the operator console.

15. The method of claim 1 wherein the step of automatically analyzing the obtained radiographic image data is accomplished by applying an analyzing algorithm.

16. A method for processing a radiographic image of a patient, executed at least in part on a host processor, comprising:

initiating exposure in response to an instruction entered from an operator console;

obtaining radiographic image data from a digital detector that is subjected to the exposure;

using a computer processor, automatically analyzing the obtained radiographic image data according to a plurality of predefined criteria for diagnostic suitability of the radiographic image, wherein diagnostic suitability of the image is with respect to image contrast, missing marker, clipped anatomy, and grid cutoff;

indicating one or more results of the diagnostic suitability analysis at the operator console, the one or more results including one or more problems with the diagnostic suitability; and automatically providing, at the operator console, a listing of one or more corrective actions based on the indicated one or more results.

\* \* \* \* \*